US007119172B2

(12) United States Patent
Pier et al.

(10) Patent No.: US 7,119,172 B2
(45) Date of Patent: Oct. 10, 2006

(54) *P. AERUGINOSA* MUCOID EXOPOLYSACCHARIDE SPECIFIC BINDING PEPTIDES

(75) Inventors: Gerald B. Pier, Brookline, MA (US); Michael J. Preston, Alan, ME (US); Lisa Cavacini, Natick, MA (US); Marshall Posner, Medfield, MA (US)

(73) Assignees: The Brigham and Women's Hospital, Inc., Boston, MA (US); Beth Israel Deaconess Medical Center, Inc., Boston, MA (US)

( * ) Notice: Subject to any disclaimer, the term of this patent is extended or adjusted under 35 U.S.C. 154(b) by 93 days.

(21) Appl. No.: 10/440,522

(22) Filed: May 16, 2003

(65) Prior Publication Data

US 2004/0091494 A1 May 13, 2004

Related U.S. Application Data

(63) Continuation-in-part of application No. 10/153,437, filed on May 21, 2002, now Pat. No. 6,962,813.

(60) Provisional application No. 60/292,365, filed on May 21, 2001.

(51) Int. Cl.
*C07K 14/00* (2006.01)
*C07K 16/00* (2006.01)
*G01N 33/53* (2006.01)
*A61K 39/395* (2006.01)

(52) U.S. Cl. .................. 530/387.1; 530/300; 530/350; 530/388.1; 435/7.1; 424/130.1

(58) Field of Classification Search ................ 530/300, 530/387.1, 388.1, 350; 435/7.1; 424/130.1
See application file for complete search history.

(56) References Cited

U.S. PATENT DOCUMENTS

| | | | |
|---|---|---|---|
| 4,578,458 | A | 3/1986 | Pier |
| 4,902,616 | A | 2/1990 | Fournier et al. |
| 5,055,455 | A | 10/1991 | Pier |
| 5,233,024 | A | 8/1993 | Schreiber et al. |
| 5,240,846 | A | 8/1993 | Collins et al. |
| 5,407,796 | A | 4/1995 | Cutting et al. |
| 5,434,086 | A | 7/1995 | Collins et al. |
| 5,502,039 | A | 3/1996 | Pier |
| 5,589,591 | A | 12/1996 | Lewis |
| 5,980,910 | A | 11/1999 | Pier |
| 5,989,542 | A | 11/1999 | Pier et al. |
| 6,245,735 | B1 | 6/2001 | Pier |
| 6,399,066 | B1 | 6/2002 | Pier |
| 6,743,431 | B1 | 6/2004 | Pier |
| 6,825,178 | B1 | 11/2004 | Pier |
| 2002/0009457 | A1 | 1/2002 | Bowersock et al. |
| 2002/0119166 | A1 | 8/2002 | Pier et al. |
| 2003/0124631 | A1 | 7/2003 | Pier et al. |
| 2004/0091494 | A1 | 5/2004 | Pier et al. |

FOREIGN PATENT DOCUMENTS

| | | |
|---|---|---|
| EP | 0 120 532 A2 | 10/1984 |
| WO | WO91/02796 | 3/1991 |
| WO | WO92/18162 | 10/1992 |
| WO | WO93/12240 | 6/1993 |
| WO | WO93/17040 | 9/1993 |
| WO | WO93/24641 | 12/1993 |
| WO | WO94/04669 | 3/1994 |
| WO | WO94/04671 | 3/1994 |
| WO | WO 94/08617 A1 | 4/1994 |
| WO | WO94/25607 | 11/1994 |
| WO | WO95/06743 | 3/1995 |
| WO | WO95/13365 | 5/1995 |
| WO | WO95/25796 | 9/1995 |
| WO | WO95/28494 | 10/1995 |
| WO | WO 02/094854 A2 | 11/2002 |

OTHER PUBLICATIONS

Albus et al., Increased levels of IgG subclasses specific for *Pseudomonas aeruginosa* exoenzyme and polysaccharide antigens in chronically infected patients with cystic fibrosis. APMIS. Dec. 1989;97(12):1146-8.
Des Jardins et al., Abstracts from the annual meeting. Am Soc Microbiol. 1989; p. 49 (abstract B-110).
Diamond et al., A cross-species analysis of the cystic fibrosis transmembrane conductance regulator. Potential functional domains and regulatory sites. J Biol Chem. Nov. 25, 1991;266(33):22761-9.
Garner et al., Immunogenic properties of *Pseudomonas aeruginosa* mucoid exopolysaccharide. Infect Immun. Jun. 1990;58(6):1835-42.
Irvin et al., Immunochemical examination of the *Pseudomonas aeruginosa* glycocalyx: a monoclonal antibody which recognizes L-guluronic acid residues of alginic acid. Can J Microbiol. Mar. 1985;31(3):268-75.
Johansen et al., Experimental immunization with *Pseudomonas aeruginosa* alginate induces IgA and IgG antibody responses. APMIS. Dec. 1991;99(12):1061-8.

(Continued)

*Primary Examiner*—Mark Navarro
(74) *Attorney, Agent, or Firm*—Wolf, Greenfield & Sacks, P.C.

(57) ABSTRACT

The present invention relates to peptides, particularly human monoclonal antibodies, that bind specifically to *P. aeruginosa* mucoid exopolysaccharide. The invention further provides methods for using these peptides in the diagnosis, prophylaxis and therapy of *P. aeruginosa* infection and related disorders (e.g., cystic fibrosis). Some antibodies of the invention enhance opsonophagocytic killing of multiple mucoid strains of *P. aeruginosa*. Compositions of these peptides, including pharmaceutical compositions, are also provided, as are functionally equivalent variants of such peptides.

39 Claims, 4 Drawing Sheets

OTHER PUBLICATIONS

Mai et al., Inhibition of adherence of mucoid *Pseudomonas aeruginosa* by alginase, specific monoclonal antibodies, and antibiotics. Infect Immun. Oct. 1993;61(10):4338-43.

Mai et al., Suppression of lymphocyte and neutrophil functions by *Pseudomonas aeruginosa* mucoid exopolysaccharide (alginate): reversal by physicochemical, alginase, and specific monoclonal antibody treatments. Infect Immun. Feb. 1993;61(2):559-64.

Meluleni et al., Comparative susceptibility of *Pseudomonas aerouginosa*. 94th Meeting of the American Society for Microbiology. 1994;94:160. Abstract E-94.

Pier et al., Rationale for development of immunotherapies that target mucoid *Pseudomonas aeruginosa* infection in cystic fibrosis patients. Behring Inst Mitt. Feb. 1997;(98):350-60.

Pier et al., Human monoclonal antibodies to *Pseudomonas aeruginosa* alginate that protect against infection by both mucoid and nonmucoid strains. J Immunol. Nov. 1, 2004;173(9):5671-8.

Pier et al., Vaccine potential of *Pseudomonas aeruginosa* mucoid exopolysaccharide (alginate). Antibiot Chemother. 1991;44:136-42.

Pier et al., Isolation and characterization of a high-molecular-weight polysaccharide from the slime of *Pseudomonas aeruginosa*. Infect. Immun. Dec. 1978;22(3):908-18.

Pier et al., Protective immunity induced in mice by immunization with high-molecular-weight polysaccharide from *Pseudomonas aeruginosa*. Infect Immun. Dec. 1978;22(3):919-25.

Pier et al., Further purification and characterization of high-molecular-weight polysaccharide from *Pseudomonas aeruginosa*. Infect Immun. Dec. 1983;42(3):936-41.

Pier et al., Analysis of naturally occurring antibodies to mucoid *Pseudomonas aeruginosa* in cystic fibrosis patients. J Infect Dis. Feb. 1996;173(2):513-5.

Pier et al., Immune complexes from immunized mice and infected cystic and fibrosis patients mediate murine and human T cell killing of hybridomas producing protective, opsonic antibody to *Pseudomonas aeruginosa*. J Clin Invest. Mar. 1993;91(3):1079-87.

Pressler et al., Immunoglobulin allotypes and IgG antibody response to *Pseudomonas aeruginosa* antigens in chronically infected cystic fibrosis patients. Clin Exp Immunol. Nov. 1992;90(2):209-14.

Saunders et al., Development of monoclonal antibodies to the mucoid exopolysaccharide of *Pseudomonas aeruginosa*. Abstr Annu Meet Am Soc Microbiol. 1986;86:45. Abstract B-129.

Theilacker et al., Construction and characterization of a *Pseudomonas aeruginosa* mucoid exopolysaccharide-alginate conjugate vaccine. Infect Immun. Jul. 2003;71(7):3875-84.

Tosi et al., Cross-sectional and longitudinal studies of naturally occurring antibodies to *Pseudomonas aeruginosa* in cystic fibrosis indicate absence of antibody-mediated protection and decline in opsonic quality after infection. J Infect Dis. Aug. 1995;172(2):453-61.

Pier et al., "Complement deposition by antibodies to *Pseudomonas aeruginosa* mucoid exopolysaccharide (MEP) and by non-MEP specific opsonins", *J. Immunology*, 147: 1869-1876, 1991.

Schreiber et al., "Induction of opsonic antibodies to *Pseudomonas aeruginosa* mucoid exopolysaccharide by an anti-idiotype monoclonal antibody", *Journal of Infectious Diseases*, 164: 507-514, 1991.

Parad et al., Pulmonary outcome of cystic fibrosis is influenced primarily by mucoid *Pseudomonas aeruginosa* infection and immune status and only modestly by genotype, *Infection and Immunity*, 67: 4744-4750; 1999.

Meluleni, et al., "Mucoid *Pseudomonas aeruginosa* growing in a biofilm in vitro are killed by opsonic antibodies to the mucoid exopolysaccharide capsule but not by antibodies produced during chronic lung infection in cystic fibrosis patients", *J. Immunology*, 155(4): 2029-38; 1995.

Preston et al., "Production and characterization of a set of mouse-human chimeric immunoglobulin G (IgG) subclass and IgA monoclonal antibodies with identical variable regions specific for *Pseudomonas aeruginosa* serogroup O6 lipopolysaccharide", *Infection and Immunity*, 66(9): 4137-4142, 1998.

Preston et al., "Prophylactic and therapeutic efficacy of immunoglobulin G antibodies to *Pseudomonas aeruginosa* lipopolysaccharide against murine experimental corneal infection", *Investigative Ophthalmology and Visual Science*, 38(7): 1418-1425, 1997. Abstract Only.

Pollack et al., "Functional properties of isotype-switched immunoglobulin M (IgM) and IgG monoclonal antibodies to *Pseudomonas aeruginosa* lipopolysaccharide", *Infection and Immunity*, 63(11): 4481-4488, 1995.

Boucher, R et al., "Gene Therapy for Cystic Fibrosis Using E1-Deleted Adenovirus: A Phase 1 Trial in the Nasal Cavity", *Human Gene Therapy*, 1994, 5:615-639.

Boyer, D et al., Poster Presentation. American Thoracic Society, #D33, May 17, 2002.

Cheng, KH et al., "Immunoglobulin A antibodies against *Pseudomonas aeruginosa* in the tear fluid of contact lens wearers", *Invest Ophthalmol Vis Sci* Sep. 1996:37 (10): 2081-8.

Ciofu, O et al., "Avidity of anti-*P aeruginosa* antibodies during chronic infection in patients with cystic fibrosis", *Thorax* 1999; 54: 141-144.

Davies, J et al., "Reduction in the adherence of *Pseudomonas aeruginosa* to native cystic fibrosis epithelium with anti-asialoGM1 antibody and neuraminidase inhibition", *Eur Respir J*, Mar. 1999; 13(3): 565-70.

De Kievit, T et al., "Monoclonal Antibodies That Distinguish Inner Core, Outer Core, and Lipid A Regions of *Pseudomonas aeruginosa* Lipopolysaccharide", Journal of Bacteriology, Dec. 1994, p. 7129-7139.

Imundo, L et al, "Cystic fibrosis epithelial cells have a receptor for pathogenic bacteria on their apical surface", *Proc. Natl. Acad. Sci. USA*, vol. 92 pp. 3019-3023, Mar. 1995.

Kropinski, A et al., "The extraction and analysis of lipopolysaccharides from *Pseudomonas aeruginosa* strain PAO, and three rough mutants", *Can. J. Mircrobiol.*, 1979, 25: 390-398.

Masoud, H et al., "General Strategy for Structural Analysis of the Oligosaccharide Region of Lipooligosaccharides. Structure of the Oligosaccharide Component of *Pseudomonas aeruginosa* IATS Serotype O6 Mutant R5 Rough-Type Lipopolysaccharide", *Biochemistry* 1994, 33, 10568-10578.

Masoud, H et al., "Structural Elucidation of the Lipopolysaccharide Core Region of the O-Chain-Deficient Mutant Strain A28 from *Pseudomonas aeruginosa* Serotype O6 (International Antigenic Typing Scheme)", *Journal of Bacteriology*, Dec. 1995, p. 6718-6726.

Meluleni, G et al., "Mucoid *Pseudomonas aeruginosa* Growing in a Biofilm In Vitro Are Killed by Opsonic Antibodies to the Mucoid Exopolysaccharide Capsule but Not by Antibodies Produced During Chronic Fibrosis Patients", *Journal of Immunology*, 1995, 155: 2029-2038.

Middleton, P. G. et al., "Nasal application of the cationic liposome DC-Chol:DOPE does not alter ion transport, lung function or bacterial growth", *Eur Respir J*, 1994, 7, 442-445.

Parad, R et al., "Pulmonary Outcome in Cystic Fibrosis Is Influenced Primarily by Mucoid *Pseudomonas aeruginosa* Infection and Immune Status and Only Modesly by Genotype", *Infection and Immunity*, Sep. 1999, p. 4744-4750.

Pennington, J et al., "Type-Specific vs. Cross-Protective Vaccinations for Gram Negative Bacterial Pneumonia", *The Journal of Infectious Diseases*, vol. 144, No. 6, Dec. 1981, p. 599-604.

Pier, G et al., "Opsonophagocytic Killing Antibody To *Pseudomonas aeruginosa* Mucoid Exopolysaccharide In Older Noncolonized Patients With Cystic Fibrosis", *N. Engl. J Med.* 1987; 317:793-8.

Pier, G et al., "Protection Agains Mucoid *Pseudomonas aeruginosa* in Rodent Models of Endobronchial Infections", *Science*, vol. 249, Aug. 1990, p. 537-540.

Pier, G et al., "Human Immune Response to *Pseudomonas aeruginosa* Mucoid Exopolysaccharide (Alginate) Vaccine", *Infection and Immunity*, Sep. 1994, p. 3972-3979.

Pier, G et al., "Role of Mutant CFTR in Hypersusceptibility of Cystic Fibrosis Patients to Lung Infections", *Science*, vol. 271, Jan. 5, 1996, p. 64-67.

Pier, G et al., "Cystic Fibrosis Transmembrane Conductance Regulator Is An Epithelial Cell Receptor For Clearance of *Pseudomonas aeruginosa* From The Lung", *Proc. Nat. Acad. Scie.*, 1997, 94:12088-93.

Pier, G et al., "Salmonella Typhi Uses CFTR To Enter Intestinal Epithelial Cells", *Nature*, 1998, 392:79-82.

Preston, M et al., "Production and Characterization of a Set of Mouse-Human Chimeric Immunoglobulin G (IgG) and IgA Monoclonal Antibodies with Identical Variable Regions Specific for *Pseudomonas aeruginosa* Serogroup O6 Lipopolysaccharide", *Infection and Immunity*, Sep. 1998, p. 4137-4142.

Reff, M et al., "Depletion of B Cells In Vivo by a Chimeric Mouse Human Monoclonal Antibody to CD20", *Blood*, vol. 83, No. 2 Jan. 15, 1994: pp. 435-445.

Riordan, J et al., "Identification of the Cystic Fibrosis Gene: Cloning and Characterization of Complimentary DNA", *Genbank*, Dec. 15, 1989, Acession No. M28668.

Riordan, J et al., "Identification of the Cystic Fibrosis Gene: Cloning and Characterization of Complimentary DNA", *Science*, 1989, 245:1066-1073.

Rowe, S.N. et al., "Structure of the Core Oligosaccharide from the Lipopolysaccharide of *Pseudomonas aeruginosa* PAC1R and Its Defective Mutants", *Eur. J. Biochem.* 132, 329-337 (1983).

Zaidi, T et al., "Cystic fibrosis Transmembrane Conductance Regulator-Mediated Corneal Epithelial Cell Ingestion of *Pseudomonas aeruginosa* is a Key Component in the Experimental Murine Keratitis", *Infect. Immun.* 1999, 67:1481-92.

Zar, H et al., "Binding of *Pseudomonas aeruginosa* to respiratory epithelial cells from patients with various mutations in the cystic fibrosis transmembrane regulator", *The Journal of Pediatrics*, 1995; 126:230-3.

Garner et al., Human immune repsonse to *Pseudomonas aeruginosa* mucoid exopolysaccharide vaccine. Clinical Research. 1987;36: Abstract 465A.

Kulseng et al., Alginate polylysine microcapsules as immune barrier: permeability of cytokines and immunoglobulins over the capsule membrane. Cell Transplant. Jul.-Aug. 1997;6(4):387-94. Abstract Only.

Pier et al., Immunochemical characterization of the mucoid exopolysaccharide of *Pseudomonas aeruginosa*. J Infect Dis. Mar. 1983;147(3):494-503. Abstract Only.

Sherbrock-Cox et al., The purification and chemical characterisation of the alginate present in extracellular material produced by mucoid strains of *Pseudomonas aeruginosa*. Carbohydr Res. Dec. 15, 1984;135(1):147-54. Abstract Only.

Thu et al., Alginate polycation microcapsules. I. Interaction between alginate and polycation. Biomaterials. May 1996;17(10):1031-40. Abstracts Only.

Gerke et al., Experimental *Pseudomonas aeruginosa* infection of the mouse cornea. Infect and Immun. Feb. 1971;3(2):209-16.

SEQUENCE LISTING

<160> NUMBER OF SEQ ID NOS: 64

<210> SEQ ID NO 1
<211> LENGTH: 369

-continued

```
<212> TYPE: DNA
<213> ORGANISM: Homo sapiens

<400> SEQUENCE: 1
cagctgcagc tgcaggagtc gggcccggga ctggtgaagc ctacggagac cctgtccctc    60
acctgcactg tctctggtgg ccccatcacc tatattaatt actactgggg ctgggtccgc   120
cagcccccag ggaaggggct ggagtggatt gggagtatcc attatgatgg gagcaccttc   180
tacaacccgt ccctcaagag tcgcgtcacc atatcaggag acacgtccaa gagcgagttc   240
tctgtgaagc tgagttctgt gaccgccgcg gacacggccg tctattactg tgcgagaacg   300
tattacgatg cttcggggag cccttacttt gaccactggg gccagggaac cctggtcacc   360
gtctcctca                                                           369

<210> SEQ ID NO 2
<211> LENGTH: 330
<212> TYPE: DNA
<213> ORGANISM: Homo sapiens

<400> SEQUENCE: 2
cagtctgtgt tgacgcagcc gccctcagtg tctgcggccc caggacagag ggtcaccatc    60
tcctgctctg gaagcagctc aaccttggg aacaattttg tatcctggta ccagcaactc   120
ccaggagcag ccccccggct cctcatttat gacaatgata agcgaccctc agggattcct   180
gaccgattct ctggctccaa gtctggcacg tcagccaccc tgggcatcac cgggctccag   240
actggggacg aggccgatta ttactgcgga acatgggata gcagcctgac tgcttatgtc   300
ttcggaagtg ggaccaaggt caccgtccta                                    330

<210> SEQ ID NO 3
<211> LENGTH: 330
<212> TYPE: DNA
<213> ORGANISM: Homo sapiens

<400> SEQUENCE: 3
cagtctgtgt tgacgcagcc gccctcagtg tctgcggccc caggacagaa ggtctccatc    60
tcctgctctg gaagcagctc aacattggg aataattatg tatcctggta ccagcagctc   120
ccaggaacag ccccccaatct cctcatttat gacaataata agcgaccctc agggattccg   180
gaccgattct ctggctccaa gtctggcacg tcagccaccc tggacatcac cggactccag   240
agtggggacg aggccgatta ttactgcgga acatgggata gcagcctgag tacttgggtg   300
ttcggcggag ggaccaaact gaccgtccta                                    330

<210> SEQ ID NO 4
<211> LENGTH: 378
<212> TYPE: DNA
<213> ORGANISM: Homo sapiens

<400> SEQUENCE: 4
cagctgcacc tgcaggagtc gggcccagga ctagtgaagc cttcggagac cctgtccctc    60
acgtgcactg tctctggtgg ccccatcacc agtaataatt actactgggg ctggatccgc   120
cagcccccag ggaaggggct ggagtggatt gggactatct cttataatgg gtacacctac   180
tacatcccgt ccctcagggg tcgagtcacc atatccggag acacgtccaa gaaccagttc   240
tccctgaggg tgaactctgt gaccgccgca gacacggcta tgtattactg tgcgagacat   300
gactatagca tgtcgtccgg acttactgac aactggttcg accccggggg ccagggaacc   360
```

```
ctggtcaccg tctcctca                                              378
```

<210> SEQ ID NO 5
<211> LENGTH: 123
<212> TYPE: PRT
<213> ORGANISM: Homo sapiens

<400> SEQUENCE: 5

```
Gln Leu Gln Leu Gln Glu Ser Gly Pro Gly Leu Val Lys Pro Thr Glu
1               5                   10                  15

Thr Leu Ser Leu Thr Cys Thr Val Ser Gly Gly Pro Ile Thr Tyr Ile
                20                  25                  30

Asn Tyr Tyr Trp Gly Trp Val Arg Gln Pro Pro Gly Lys Gly Leu Glu
            35                  40                  45

Trp Ile Gly Ser Ile His Tyr Asp Gly Ser Thr Phe Tyr Asn Pro Ser
        50                  55                  60

Leu Lys Ser Arg Val Thr Ile Ser Gly Asp Thr Ser Lys Ser Glu Phe
65                  70                  75                  80

Ser Val Lys Leu Ser Ser Val Thr Ala Ala Asp Thr Ala Val Tyr Tyr
                85                  90                  95

Cys Ala Arg Thr Tyr Tyr Asp Ala Ser Gly Ser Pro Tyr Phe Asp His
                100                 105                 110

Trp Gly Gln Gly Thr Leu Val Thr Val Ser Ser
            115                 120
```

<210> SEQ ID NO 6
<211> LENGTH: 109
<212> TYPE: PRT
<213> ORGANISM: Homo sapiens

<400> SEQUENCE: 6

```
Gln Ser Val Leu Thr Gln Pro Pro Ser Val Ser Ala Ala Pro Gly Gln
1               5                   10                  15

Arg Val Thr Ile Ser Cys Ser Gly Ser Ser Ser Asn Leu Gly Asn Asn
                20                  25                  30

Phe Val Ser Trp Tyr Gln Gln Leu Pro Gly Ala Ala Pro Arg Leu Leu
            35                  40                  45

Ile Tyr Asp Asn Asp Lys Arg Pro Ser Gly Ile Pro Asp Arg Phe Ser
        50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Ser Ser Leu
                85                  90                  95

Thr Ala Tyr Val Phe Gly Ser Gly Thr Lys Val Thr Val
                100                 105
```

<210> SEQ ID NO 7
<211> LENGTH: 110
<212> TYPE: PRT
<213> ORGANISM: Homo sapiens

<400> SEQUENCE: 7

```
Gln Ser Val Leu Thr Gln Pro Pro Ser Val Ser Ala Ala Pro Gly Gln
1               5                   10                  15

Lys Val Ser Ile Ser Cys Ser Gly Ser Ser Ser Asn Ile Gly Asn Asn
                20                  25                  30

Tyr Val Ser Trp Tyr Gln Gln Leu Pro Gly Thr Ala Pro Asn Leu Leu
            35                  40                  45
```

```
Ile Tyr Asp Asn Asn Lys Arg Pro Ser Gly Ile Pro Asp Arg Phe Ser
            50                  55                  60

Gly Ser Lys Ser Gly Thr Ser Ala Thr Leu Asp Ile Thr Gly Leu Gln
 65                  70                  75                  80

Ser Gly Asp Glu Ala Asp Tyr Tyr Cys Gly Thr Trp Asp Ser Ser Leu
                 85                  90                  95

Ser Thr Trp Val Phe Gly Gly Gly Thr Lys Leu Thr Val Leu
            100                 105                 110

<210> SEQ ID NO 8
<211> LENGTH: 126
<212> TYPE: PRT
<213> ORGANISM: Homo sapiens

<400> SEQUENCE: 8

Gln Leu His Leu Gln Glu Ser Gly Pro Gly Leu Val Lys Pro Ser Glu
 1               5                  10                  15

Thr Leu Ser Leu Thr Cys Thr Val Ser Gly Pro Ile Thr Ser Asn
             20                  25                  30

Asn Tyr Tyr Trp Gly Trp Ile Arg Gln Pro Pro Gly Lys Gly Leu Glu
             35                  40                  45

Trp Ile Gly Thr Ile Ser Tyr Asn Gly Tyr Thr Tyr Tyr Ile Pro Ser
            50                  55                  60

Leu Arg Gly Arg Val Thr Ile Ser Gly Asp Thr Ser Lys Asn Gln Phe
 65                  70                  75                  80

Ser Leu Arg Val Asn Ser Val Thr Ala Ala Asp Thr Ala Met Tyr Tyr
                 85                  90                  95

Cys Ala Arg His Asp Tyr Ser Met Ser Ser Gly Leu Thr Asp Asn Trp
            100                 105                 110

Phe Asp Pro Trp Gly Gln Gly Thr Leu Val Thr Val Ser Ser
            115                 120                 125

<210> SEQ ID NO 9
<211> LENGTH: 21
<212> TYPE: DNA
<213> ORGANISM: Homo sapiens

<400> SEQUENCE: 9
tatattaatt actactgggg c                                          21

<210> SEQ ID NO 10
<211> LENGTH: 48
<212> TYPE: DNA
<213> ORGANISM: Homo sapiens

<400> SEQUENCE: 10
agtatccatt atgatgggag caccttctac aacccgtccc tcaagagt             48

<210> SEQ ID NO 11
<211> LENGTH: 39
<212> TYPE: DNA
<213> ORGANISM: Homo sapiens

<400> SEQUENCE: 11
acgtattacg atgcttcggg gagcccttac tttgaccac                       39

<210> SEQ ID NO 12
<211> LENGTH: 39
<212> TYPE: DNA
```

<213> ORGANISM: Homo sapiens

<400> SEQUENCE: 12
tctggaagca gctccaacct tgggaacaat tttgtatcc        39

<210> SEQ ID NO 13
<211> LENGTH: 21
<212> TYPE: DNA
<213> ORGANISM: Homo sapiens

<400> SEQUENCE: 13
gacaatgata agcgaccctc a        21

<210> SEQ ID NO 14
<211> LENGTH: 33
<212> TYPE: DNA
<213> ORGANISM: Homo sapiens

<400> SEQUENCE: 14
ggaacatggg atagcagcct gactgcttat gtc        33

<210> SEQ ID NO 15
<211> LENGTH: 39
<212> TYPE: DNA
<213> ORGANISM: Homo sapiens

<400> SEQUENCE: 15
tctggaagca gctccaacat tgggaataat tatgtatcc        39

<210> SEQ ID NO 16
<211> LENGTH: 21
<212> TYPE: DNA
<213> ORGANISM: Homo sapiens

<400> SEQUENCE: 16
gacaataata agcgaccctc a        21

<210> SEQ ID NO 17
<211> LENGTH: 33
<212> TYPE: DNA
<213> ORGANISM: Homo sapiens

<400> SEQUENCE: 17
ggaacatggg atagcagcct gagtacttgg gtg        33

<210> SEQ ID NO 18
<211> LENGTH: 21
<212> TYPE: DNA
<213> ORGANISM: Homo sapiens

<400> SEQUENCE: 18
agtaataatt actactgggg c        21

<210> SEQ ID NO 19
<211> LENGTH: 48
<212> TYPE: DNA
<213> ORGANISM: Homo sapiens

<400> SEQUENCE: 19
actatctctt ataatgggta cacctactac atcccgtccc tcagggt        48

<210> SEQ ID NO 20
<211> LENGTH: 48

<212> TYPE: DNA
<213> ORGANISM: Homo sapiens

<400> SEQUENCE: 20
catgactata gcatgtcgtc cggacttact gacaactggt tcgacccc         48

<210> SEQ ID NO 21
<211> LENGTH: 7
<212> TYPE: PRT
<213> ORGANISM: Homo sapiens

<400> SEQUENCE: 21

Tyr Ile Asn Tyr Tyr Trp Gly
1               5

<210> SEQ ID NO 22
<211> LENGTH: 16
<212> TYPE: PRT
<213> ORGANISM: Homo sapiens

<400> SEQUENCE: 22

Ser Ile His Tyr Asp Gly Ser Thr Phe Tyr Asn Pro Ser Leu Lys Ser
1               5                   10                  15

<210> SEQ ID NO 23
<211> LENGTH: 13
<212> TYPE: PRT
<213> ORGANISM: Homo sapiens

<400> SEQUENCE: 23

Thr Tyr Tyr Asp Ala Ser Gly Ser Pro Tyr Phe Asp His
1               5                   10

<210> SEQ ID NO 24
<211> LENGTH: 13
<212> TYPE: PRT
<213> ORGANISM: Homo sapiens

<400> SEQUENCE: 24

Ser Gly Ser Ser Ser Asn Leu Gly Asn Asn Phe Val Ser
1               5                   10

<210> SEQ ID NO 25
<211> LENGTH: 7
<212> TYPE: PRT
<213> ORGANISM: Homo sapiens

<400> SEQUENCE: 25

Asp Asn Asp Lys Arg Pro Ser
1               5

<210> SEQ ID NO 26
<211> LENGTH: 11
<212> TYPE: PRT
<213> ORGANISM: Homo sapiens

<400> SEQUENCE: 26

Gly Thr Trp Asp Ser Ser Leu Thr Ala Tyr Val
1               5                   10

<210> SEQ ID NO 27
<211> LENGTH: 13
<212> TYPE: PRT
<213> ORGANISM: Homo sapiens -continued

<400> SEQUENCE: 27

Ser Gly Ser Ser Ser Asn Ile Gly Asn Asn Tyr Val Ser
1               5                   10

<210> SEQ ID NO 28
<211> LENGTH: 7
<212> TYPE: PRT
<213> ORGANISM: Homo sapiens

<400> SEQUENCE: 28

Asp Asn Asn Lys Arg Pro Ser
1               5

<210> SEQ ID NO 29
<211> LENGTH: 11
<212> TYPE: PRT
<213> ORGANISM: Homo sapiens

<400> SEQUENCE: 29

Gly Thr Trp Asp Ser Ser Leu Ser Thr Trp Val
1               5                   10

<210> SEQ ID NO 30
<211> LENGTH: 7
<212> TYPE: PRT
<213> ORGANISM: Homo sapiens

<400> SEQUENCE: 30

Ser Asn Asn Tyr Tyr Trp Gly
1               5

<210> SEQ ID NO 31
<211> LENGTH: 16
<212> TYPE: PRT
<213> ORGANISM: Homo sapiens

<400> SEQUENCE: 31

Thr Ile Ser Tyr Asn Gly Tyr Thr Tyr Tyr Ile Pro Ser Leu Arg Gly
1               5                   10                  15

<210> SEQ ID NO 32
<211> LENGTH: 16
<212> TYPE: PRT
<213> ORGANISM: Homo sapiens

<400> SEQUENCE: 32

His Asp Tyr Ser Met Ser Ser Gly Leu Thr Asp Asn Trp Phe Asp Pro
1               5                   10                  15

<210> SEQ ID NO 33
<211> LENGTH: 90
<212> TYPE: DNA
<213> ORGANISM: Homo sapiens

<400> SEQUENCE: 33
cagctgcagc tgcaggagtc gggccccgga ctggtgaagc ctacggagac cctgtccctc    60
acctgcactg tctctggtgg ccccatcacc                                    90

<210> SEQ ID NO 34
<211> LENGTH: 42
<212> TYPE: DNA
<213> ORGANISM: Homo sapiens

<400> SEQUENCE: 34
tgggtccgcc agccccagg gaagggctg gagtggattg gg                    42

<210> SEQ ID NO 35
<211> LENGTH: 96
<212> TYPE: DNA
<213> ORGANISM: Homo sapiens

<400> SEQUENCE: 35
cgcgtcacca tatcaggaga cacgtccaag agcgagttct ctgtgaagct gagttctgtg    60
accgccgcgg acacggccgt ctattactgt gcgaga                            96

<210> SEQ ID NO 36
<211> LENGTH: 33
<212> TYPE: DNA
<213> ORGANISM: Homo sapiens

<400> SEQUENCE: 36
tggggccagg gaaccctggt caccgtctcc tca                               33

<210> SEQ ID NO 37
<211> LENGTH: 66
<212> TYPE: DNA
<213> ORGANISM: Homo sapiens

<400> SEQUENCE: 37
cagtctgtgt tgacgcagcc gccctcagtg tctgcggccc caggacagag ggtcaccatc    60
tcctgc                                                             66

<210> SEQ ID NO 38
<211> LENGTH: 45
<212> TYPE: DNA
<213> ORGANISM: Homo sapiens

<400> SEQUENCE: 38
tggtaccagc aactcccagg agcagccccc cggctcctca tttat                  45

<210> SEQ ID NO 39
<211> LENGTH: 96
<212> TYPE: DNA
<213> ORGANISM: Homo sapiens

<400> SEQUENCE: 39
gggattcctg accgattctc tggctccaag tctggcacgt cagccaccct gggcatcacc    60
gggctccaga ctggggacga ggccgattat tactgc                            96

<210> SEQ ID NO 40
<211> LENGTH: 30
<212> TYPE: DNA
<213> ORGANISM: Homo sapiens

<400> SEQUENCE: 40
ttcggaagtg ggaccaaggt caccgtccta                                   30

<210> SEQ ID NO 41
<211> LENGTH: 66
<212> TYPE: DNA
<213> ORGANISM: Homo sapiens

<400> SEQUENCE: 41
cagtctgtgt tgacgcagcc gccctcagtg tctgcggccc caggacagaa ggtctccatc    60

-continued

| | |
|---|---|
| tcctgc | 66 |

<210> SEQ ID NO 42
<211> LENGTH: 45
<212> TYPE: DNA
<213> ORGANISM: Homo sapiens

<400> SEQUENCE: 42

| | |
|---|---|
| tggtaccagc agctcccagg aacagccccc aatctcctca tttat | 45 |

<210> SEQ ID NO 43
<211> LENGTH: 96
<212> TYPE: DNA
<213> ORGANISM: Homo sapiens

<400> SEQUENCE: 43

| | |
|---|---|
| gggattccgg accgattctc tgctccaag tctggcacgt cagccaccct ggacatcacc | 60 |
| ggactccaga gtggggacga ggccgattat tactgc | 96 |

<210> SEQ ID NO 44
<211> LENGTH: 30
<212> TYPE: DNA
<213> ORGANISM: Homo sapiens

<400> SEQUENCE: 44

| | |
|---|---|
| ttcggcggag ggaccaaact gaccgtccta | 30 |

<210> SEQ ID NO 45
<211> LENGTH: 90
<212> TYPE: DNA
<213> ORGANISM: Homo sapiens

<400> SEQUENCE: 45

| | |
|---|---|
| cagctgcacc tgcaggagtc gggcccagga ctagtgaagc cttcggagac cctgtccctc | 60 |
| acgtgcactg tctctggtgg ccccatcacc | 90 |

<210> SEQ ID NO 46
<211> LENGTH: 42
<212> TYPE: DNA
<213> ORGANISM: Homo sapiens

<400> SEQUENCE: 46

| | |
|---|---|
| tggatccgcc agcccccagg gaaggggctg gagtggattg gg | 42 |

<210> SEQ ID NO 47
<211> LENGTH: 95
<212> TYPE: DNA
<213> ORGANISM: Homo sapiens

<400> SEQUENCE: 47

| | |
|---|---|
| cgagtcacca tatccggaga cacgtccaag aaccagttct ccctgagggt gaactctgtg | 60 |
| accgccgcag acacggctat gtattactgt gcgag | 95 |

<210> SEQ ID NO 48
<211> LENGTH: 33
<212> TYPE: DNA
<213> ORGANISM: Homo sapiens

<400> SEQUENCE: 48

| | |
|---|---|
| tggggccagg gaaccctggt caccgtctcc tca | 33 |

```
<210> SEQ ID NO 49
<211> LENGTH: 30
<212> TYPE: PRT
<213> ORGANISM: Homo sapiens

<400> SEQUENCE: 49

Gln Leu Gln Leu Gln Glu Ser Gly Pro Gly Leu Val Lys Pro Thr Glu
1               5                   10                  15

Thr Leu Ser Leu Thr Cys Thr Val Ser Gly Gly Pro Ile Thr
            20                  25                  30

<210> SEQ ID NO 50
<211> LENGTH: 14
<212> TYPE: PRT
<213> ORGANISM: Homo sapiens

<400> SEQUENCE: 50

Trp Val Arg Gln Pro Pro Gly Lys Gly Leu Glu Trp Ile Gly
1               5                   10

<210> SEQ ID NO 51
<211> LENGTH: 32
<212> TYPE: PRT
<213> ORGANISM: Homo sapiens

<400> SEQUENCE: 51

Arg Val Thr Ile Ser Gly Asp Thr Ser Lys Ser Glu Phe Ser Val Lys
1               5                   10                  15

Leu Ser Ser Val Thr Ala Ala Asp Thr Ala Val Tyr Tyr Cys Ala Arg
            20                  25                  30

<210> SEQ ID NO 52
<211> LENGTH: 11
<212> TYPE: PRT
<213> ORGANISM: Homo sapiens

<400> SEQUENCE: 52

Trp Gly Gln Gly Thr Leu Val Thr Val Ser Ser
1               5                   10

<210> SEQ ID NO 53
<211> LENGTH: 22
<212> TYPE: PRT
<213> ORGANISM: Homo sapiens

<400> SEQUENCE: 53

Gln Ser Val Leu Thr Gln Pro Pro Ser Val Ser Ala Ala Pro Gly Gln
1               5                   10                  15

Arg Val Thr Ile Ser Cys
            20

<210> SEQ ID NO 54
<211> LENGTH: 15
<212> TYPE: PRT
<213> ORGANISM: Homo sapiens

<400> SEQUENCE: 54

Trp Tyr Gln Gln Leu Pro Gly Ala Ala Pro Arg Leu Leu Ile Tyr
1               5                   10                  15

<210> SEQ ID NO 55
<211> LENGTH: 32
<212> TYPE: PRT
<213> ORGANISM: Homo sapiens
```

```
<400> SEQUENCE: 55

Gly Ile Pro Asp Arg Phe Ser Gly Ser Lys Ser Gly Thr Ser Ala Thr
1               5                   10                  15

Leu Gly Ile Thr Gly Leu Gln Thr Gly Asp Glu Ala Asp Tyr Tyr Cys
            20                  25                  30

<210> SEQ ID NO 56
<211> LENGTH: 9
<212> TYPE: PRT
<213> ORGANISM: Homo sapiens

<400> SEQUENCE: 56

Phe Gly Ser Gly Thr Lys Val Thr Val
1               5

<210> SEQ ID NO 57
<211> LENGTH: 22
<212> TYPE: PRT
<213> ORGANISM: Homo sapiens

<400> SEQUENCE: 57

Gln Ser Val Leu Thr Gln Pro Pro Ser Val Ser Ala Ala Pro Gly Gln
1               5                   10                  15

Lys Val Ser Ile Ser Cys
            20

<210> SEQ ID NO 58
<211> LENGTH: 15
<212> TYPE: PRT
<213> ORGANISM: Homo sapiens

<400> SEQUENCE: 58

Trp Tyr Gln Gln Leu Pro Gly Thr Ala Pro Asn Leu Leu Ile Tyr
1               5                   10                  15

<210> SEQ ID NO 59
<211> LENGTH: 32
<212> TYPE: PRT
<213> ORGANISM: Homo sapiens

<400> SEQUENCE: 59

Gly Ile Pro Asp Arg Phe Ser Gly Ser Lys Ser Gly Thr Ser Ala Thr
1               5                   10                  15

Leu Asp Ile Thr Gly Leu Gln Ser Gly Asp Glu Ala Asp Tyr Tyr Cys
            20                  25                  30

<210> SEQ ID NO 60
<211> LENGTH: 10
<212> TYPE: PRT
<213> ORGANISM: Homo sapiens

<400> SEQUENCE: 60

Phe Gly Gly Gly Thr Lys Leu Thr Val Leu
1               5                   10

<210> SEQ ID NO 61
<211> LENGTH: 30
<212> TYPE: PRT
<213> ORGANISM: Homo sapiens

<400> SEQUENCE: 61

Gln Leu His Leu Gln Glu Ser Gly Pro Gly Leu Val Lys Pro Ser Glu
```

```
                1               5                  10                 15
Thr Leu Ser Leu Thr Cys Thr Val Ser Gly Gly Pro Ile Thr
                20                 25                 30

<210> SEQ ID NO 62
<211> LENGTH: 14
<212> TYPE: PRT
<213> ORGANISM: Homo sapiens

<400> SEQUENCE: 62

Trp Ile Arg Gln Pro Pro Gly Lys Gly Leu Glu Trp Ile Gly
1               5                   10

<210> SEQ ID NO 63
<211> LENGTH: 32
<212> TYPE: PRT
<213> ORGANISM: Homo sapiens

<400> SEQUENCE: 63

Arg Val Thr Ile Ser Gly Asp Thr Ser Lys Asn Gln Phe Ser Leu Arg
1               5                   10                  15

Val Asn Ser Val Thr Ala Ala Asp Thr Ala Met Tyr Tyr Cys Ala Arg
                20                  25                  30

<210> SEQ ID NO 64
<211> LENGTH: 11
<212> TYPE: PRT
<213> ORGANISM: Homo sapiens

<400> SEQUENCE: 64

Trp Gly Gln Gly Thr Leu Val Thr Val Ser Ser
1               5                   10
```

P. AERUGINOSA MUCOID EXOPOLYSACCHARIDE SPECIFIC BINDING PEPTIDES

RELATED APPLICATIONS

This application is a continuation-in-part of U.S. non-provisional application filed May 21, 2002, entitled "P. AERUGINOSA MUCOID EXOPOLYSACCHARIDE SPECIFIC BINDING PEPTIDES", having Ser. No. 10/153,437, now U.S. Pat. No. 6,962,813, which claims priority to U.S. Provisional Patent Application filed May 21, 2001, entitled "P. AERUGINOSA MUCOID EXOPOLYSACCHARIDE SPECIFIC BINDING PEPTIDES", having Ser. No. 60/292,365, the contents of which are incorporated by reference herein in their entirety.

GOVERNMENT SUPPORT

This work was funded in part by grant number HL-58346, from the National Institutes of Health. Accordingly, the United States Government may have certain rights to this invention.

FIELD OF THE INVENTION

This invention relates generally to prevention and treatment of Pseudomonas aeruginosa (P. aeruginosa) infections and related disorders (e.g., cystic fibrosis) using peptides, including human monoclonal antibodies, that bind to mucoid exopolysaccharide (MEP) of P. aeruginosa.

BACKGROUND OF THE INVENTION

P. aeruginosa is an opportunistic organism capable of colonizing skin, ear, lung and bowel. In healthy individuals, such colonization does not normally cause a problem. However, if the individual also has an underlying disorder or condition that compromises their immunity, then infection can be serious. Examples of such disorders or conditions include chemotherapy-induced immunosuppression, diabetes mellitus, cancer, AIDS and cystic fibrosis. It has been estimated that more than 70% of patients with cystic fibrosis are infected with P. aeruginosa. In these patients, P. aeruginosa infection is associated with chronic obstructive bronchitis.

Colonization of P. aeruginosa begins with attachment of the bacterium to epithelial tissues (e.g., lung epithelia). Mucoid strains of P. aeruginosa produce a mucoid exopolysaccharide (i.e., MEP or alginate) which is used by the bacterium throughout the infection. MEP is a polymer of uronic acids.

The bacterium can be relatively resistant to antibiotic therapy and innate and adaptive immune mechanisms, including antibody and complement mediated pathways. MEP is believed to be a contributing factor to immune resistance of the microbe.

SUMMARY OF THE INVENTION

The present invention relates generally to the identification and use of peptides that bind to P. aeruginosa mucoid exopolysaccharide (MEP). Peptides utilizing the variable region sequences described herein include polypeptides, monoclonal antibodies (such as human monoclonal antibodies), and antibody fragments. A common feature of the peptides disclosed herein is their ability to recognize and bind to P. aeruginosa MEP specifically. An important characteristic of some of the antibodies and antibody fragments provided by the invention is their ability to enhance opsonization and phagocytosis (i.e., opsonophagocytosis) of P. aeruginosa.

In one aspect, the invention provides a composition that comprises an isolated peptide or a functionally equivalent variant thereof that binds, preferably selectively, to P. aeruginosa MEP and which comprises an amino acid sequence of a P. aeruginosa MEP-binding complementarity determining region (CDR). The P. aeruginosa MEP-binding CDR may be selected from the group of heavy and light chain CDRs derived from the antibodies of the invention. Each heavy and light chain possesses three separate CDRs, namely CDR1, CDR2 and CDR3. Thus, the P. aeruginosa MEP-binding CDR may be a P. aeruginosa MEP-binding CDR3, or a P. aeruginosa MEP-binding CDR2, or a P. aeruginosa MEP-binding CDR1. These CDRs comprise amino acid sequences selected from the group consisting of SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31 and SEQ ID NO:32.

SEQ ID NO:21, SEQ ID NO:22, SEQ ID NO:23, SEQ ID NO:30, SEQ ID NO:31 and SEQ ID NO:32 are amino acid sequences of CDRs derived from P. aeruginosa MEP-binding heavy chain variable regions disclosed herein. SEQ ID NO:24, SEQ ID NO:25, SEQ ID NO:26, SEQ ID NO:27, SEQ ID NO:28 and SEQ ID NO:29 are amino acid sequences of CDRs derived from P. aeruginosa MEP-binding light chain variable regions disclosed herein.

The invention embraces a number of different embodiments relating to the foregoing isolated peptides. The isolated peptides preferably comprise a P. aeruginosa MEP-binding CDR. In one embodiment, the P. aeruginosa MEP-binding CDR is a P. aeruginosa MEP-binding CDR3. The CDR3 may be a light chain CDR3 or a heavy chain CDR3. Such CDR3 amino acid sequences are selected from the group consisting of SEQ ID NO:23, SEQ ID NO:26, SEQ ID NO:29 and SEQ ID NO:32. Amino acid sequences of heavy chain CDR3 include SEQ ID NO:23 and SEQ ID NO:32. Amino acid sequences of light chain CDR3 include SEQ ID NO:26 and SEQ ID NO:29. In another embodiment, the isolated peptide comprises an amino acid sequence of a light chain CDR3 and an amino acid sequence of a heavy chain CDR3.

In another embodiment, the P. aeruginosa MEP-binding CDR is a P. aeruginosa MEP-binding CDR2. The CDR2 may be a light chain CDR2 or a heavy chain CDR2. Such CDR2 amino acid sequences are selected from the group consisting of SEQ ID NO:22, SEQ ID NO:25, SEQ ID NO:28 and SEQ ID NO:31. Amino acid sequences of heavy chain CDR2 include SEQ ID NO:22 and SEQ ID NO:31. Amino acid sequences of light chain CDR2 include SEQ ID NO:25 and SEQ ID NO:28. In another embodiment, the isolated peptide comprises an amino acid sequence of a light chain CDR2 and an amino acid sequence of a heavy chain CDR2.

In yet another embodiment, the P. aeruginosa MEP-binding CDR is a P. aeruginosa MEP-binding CDR1. The CDR1 may be a light chain CDR1 or a heavy chain CDR1. Such CDR1 amino acid sequences are selected from the group consisting of SEQ ID NO:21, SEQ ID NO:24, SEQ ID NO:27 and SEQ ID NO:30. Amino acid sequences of heavy chain CDR1 include SEQ ID NO:21 and SEQ ID NO:30. Amino acid sequences of light chain CDR1 include SEQ ID NO:24 and SEQ ID NO:27. In another embodiment, the isolated peptide comprises an amino acid sequence of a light chain CDR1 and an amino acid sequence of a heavy chain CDR1.

The invention also intends to embrace isolated peptides which comprise any combination of the disclosed amino acid sequences of heavy and light chain CDR1, CDR2 and CDR3, provided the isolated peptide binds to P. aeruginosa MEP. In important embodiments, the isolated peptide binds selectively to P. aeruginosa MEP.

In one embodiment, the isolated peptide comprises an amino acid sequence of a heavy or light chain variable region of an antibody disclosed herein. In important embodiments, the amino acid sequences are selected from the group consisting of SEQ ID NO:5, SEQ ID NO:6, SEQ ID NO:7 and SEQ ID NO:8. SEQ ID NO:5 and SEQ ID NO:8 are amino acid sequences of heavy chain variable regions of the P. aeruginosa MEP-binding antibodies disclosed herein. SEQ ID NO:6 and SEQ ID NO:7 are amino acid sequences of light chain variable regions of the P. aeruginosa MEP-binding antibodies disclosed herein. These heavy and light chain variable region sequences contain sequence of both framework and CDRs, as described in the Examples.

In one embodiment, the isolated peptide comprises an amino acid sequence of a CDR derived from a MEP-binding heavy chain variable region and an amino acid sequence of a CDR derived from a MEP-binding light chain variable region.

In one embodiment, the isolated peptide is an isolated antibody or antibody fragment. The isolated antibody or antibody fragment may be an isolated intact soluble monoclonal antibody. The isolated antibody or antibody fragment may be an isolated monoclonal antibody fragment selected from the group consisting of an $F(ab')_2$ fragment, an Fd fragment, and an Fab fragment. In preferred embodiments, the isolated antibody or antibody fragment enhances opsonophagocytosis of P. aeruginosa. Such an antibody or antibody fragment is referred to herein as "an opsonic antibody or antibody fragment". In an important embodiment, the isolated antibody or antibody fragment comprises an Fc domain in addition to comprising one or more P. aeruginosa MEP-binding CDR. Accordingly, in some embodiments, the isolated antibody or antibody fragment comprises one or more P. aeruginosa MEP-binding CDR and enhances opsonophagocytosis of P. aeruginosa.

In some embodiments, particularly those in which the isolated peptide is an antibody or an antibody fragment, the peptide comprises two amino acid sequences selected from the group consisting of heavy and light chain variable region amino acid sequences, i.e., SEQ ID NO:5, SEQ ID NO:6, SEQ ID NO:7, and SEQ ID NO:8. In some preferred embodiments, the isolated antibody or antibody fragment comprises one heavy chain variable region amino acid sequence selected from the group consisting of SEQ ID NO:5 and SEQ ID NO:8, and one light chain variable region amino acid sequence selected from the group consisting of SEQ ID NO:6 and SEQ ID NO:7. In certain embodiments, the isolated antibody or antibody fragment comprises a heavy chain variable region having an amino acid sequence of SEQ ID NO:5 and a light chain variable region having an amino acid sequence of SEQ ID NO:6. In other embodiments, the isolated antibody or antibody fragment comprises a heavy chain variable region having an amino acid sequence of SEQ ID NO:5 and a light chain variable region having an amino acid sequence of SEQ ID NO:7. In still other embodiments, the isolated antibody or antibody fragment comprises a heavy chain variable region having an amino acid sequence of SEQ ID NO:8 and a light chain variable region having an amino acid sequence of SEQ ID NO:6. And in still further embodiments, the isolated antibody or antibody fragment comprises a heavy chain variable region having an amino acid sequence of SEQ ID NO:8 and a light chain variable region having an amino acid sequence of SEQ ID NO:7. The antibody and antibody fragments of the invention similarly may comprise one or more of the P. aeruginosa MEP-binding CDRs disclosed herein, or functionally equivalent variants thereof.

The peptides of the invention, including antibodies and antibody fragments, have particular utility in the detection of P. aeruginosa bacteria, the diagnosis of P. aeruginosa infection and the prevention and treatment of such infections and the disorders with which they are associated.

Accordingly, in another aspect, the invention provides a method for detecting P. aeruginosa in a subject. The method involves determining a level of binding of an isolated peptide or a functionally equivalent variant thereof to a sample in or from a subject (i.e., a test level of binding), and comparing the test level of binding to a control. The isolated peptide selectively binds to P. aeruginosa MEP (i.e., a MEP-binding peptide) and comprises a P. aeruginosa MEP-binding CDR, or a functionally equivalent variant thereof. The P. aeruginosa MEP-binding CDR may be selected from the group consisting of light chain or heavy chain CDRs, as described above. A test level of binding that is greater than the control is indicative of P. aeruginosa in the sample, and thus in the subject. The control is the level of binding of the peptide to a control sample in or from a subject that is known to be negative for P. aeruginosa. In one embodiment, the test level of binding is measured in vitro, and involves the harvest of a sample from the subject. Alternatively, the test level of binding is measured in vivo, and involves administering the isolated peptide to the subject, preferably in a pharmaceutical composition as described herein. Even more preferably, the peptide is conjugated to a detectable label or a label capable of being detected (e.g., biotin or avidin). In one embodiment, the subject is at risk of developing a P. aeruginosa infection. In another embodiment, the subject has cystic fibrosis. The peptide may be an antibody or antibody fragment, which may in turn enhance opsonophagocytosis, but it is not so limited.

In yet a further aspect, the invention provides a method for treating a subject having, or at risk of developing, a P. aeruginosa infection. The method involves administering to a subject in need of such treatment an isolated peptide or a functionally equivalent variant thereof that binds, preferably selectively, to P. aeruginosa MEP, and comprises a P. aeruginosa MEP-binding CDR. The CDR comprises an amino acid sequence of a light chain or heavy chain CDR of the antibodies of the invention, as described above. The isolated peptide is administered to the subject in an amount effective to inhibit a P. aeruginosa infection. In one embodiment, the subject has cystic fibrosis. In an important embodiment, the isolated peptide is an isolated antibody or antibody fragment. In a preferred embodiment, the isolated antibody or antibody fragment is capable of opsonophagocytosis of P. aeruginosa. In some embodiments, more than one such peptide is administered to a subject.

In another aspect of the invention, the isolated peptide can be used in the delivery of, for example, imaging or cytotoxic agents to P. aeruginosa colonies or individual bacteria in vivo. In some embodiments, the peptides can be conjugated to agents such as but not limited to antibiotics. In other embodiments, the peptide may be conjugated to a cytotoxic agent (e.g., a bactericide) allowing the agent to be delivered to a *P. aeruginosa* bacterium or bacterial colony upon in vivo administration of the peptide.

In a related aspect, the invention provides a method for treating a subject having, or at risk of developing, a *P. aeruginosa* related disorder (i.e., a disorder related to or associated with a *P. aeruginosa* infection). The method involves administering to a subject in need of such treatment an isolated peptide of the invention, or a functionally equivalent variant thereof, in an effective amount to inhibit the *P. aeruginosa* related disorder. A *P. aeruginosa* related disorder may be selected from the group of disorders consisting of cystic fibrosis, ulcerative keratitis, pneumonia, bacteremia, organ infection such as kidney, bladder, liver, brain, skin, muscle, lymph node or sinus infection. In an important embodiment, the isolated peptide is an isolated antibody or antibody fragment. In a preferred embodiment, the isolated antibody or antibody fragment is capable of opsonophagocytosis of *P. aeruginosa*.

In certain embodiments of the treatment methods provided herein, the isolated peptide is co-administered with another therapeutic agent. The therapeutic agent may be one that is used prophylactically or therapeutically in a *P. aeruginosa* infection, such as for example an antibiotic. Alternatively, it may be an agent that is used in the treatment of a *P. aeruginosa* related disorder, such as for example N-acetyl cysteine or DNase which are used in the treatment of cystic fibrosis. When administered in conjunction with an antibiotic, the isolated peptide can enhance the cytocidal effect of the antibiotic by facilitating entry of the antibiotic into a *P. aeruginosa* colony. This is especially the case where the peptide is an antibody or an antibody fragment that enhances opsonophagocytosis. In some embodiments, the treatment methods involve administering synergistic amounts of the isolated peptide and the other therapeutic agent.

In yet another aspect, the invention provides pharmaceutical compositions that comprise one or more of the foregoing isolated peptides, such as one or more of the foregoing isolated antibodies or antibody fragments, or a functionally equivalent variant, thereof and a pharmaceutically acceptable carrier. In one embodiment, the pharmaceutical composition comprises a peptide that is an isolated antibody or antibody fragment that binds to *P. aeruginosa* MEP, and enhances opsonophagocytosis of *P. aeruginosa*. The isolated peptide may be conjugated to a number of compounds including but not limited to detectable labels and cytotoxic agents. In some important embodiments, the isolated peptide is present in a prophylactically or therapeutically effective amount. In another embodiment, the isolated peptide is present in an effective amount for detecting *P. aeruginosa* in a sample in or from a subject. In a related aspect, the invention provides a method for manufacturing a medicament comprising contacting an isolated peptide of the invention with a pharmaceutically acceptable carrier.

In a further aspect, the invention provides an isolated nucleic acid molecule comprising a nucleotide sequence that codes for a *P. aeruginosa* MEP-binding CDR. The CDR may be a CDR1, CDR2 or CDR3 from the heavy or light chains of the antibodies of the invention. In one embodiment, the isolated nucleic acid molecule comprises a nucleotide sequence selected from the group consisting of SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19 and SEQ ID NO:20. SEQ ID NO:9, SEQ ID NO:10, SEQ ID NO:11, SEQ ID NO:18, SEQ ID NO:19 and SEQ ID NO:20 are nucleotide sequences of heavy chain CDR. SEQ ID NO:12, SEQ ID NO:13, SEQ ID NO:14, SEQ ID NO:15, SEQ ID NO:16 and SEQ ID NO:17 are nucleotide sequences of light chain CDR. In another embodiment, the isolated nucleic acid molecule comprises a nucleotide sequence selected from the group consisting of SEQ ID NO:1, SEQ ID NO:2, SEQ ID NO:3, and SEQ ID NO:4. Isolated nucleic acid molecules comprising a nucleotide sequence that encodes a *P. aeruginosa* MEP-binding peptide having an amino acid sequence selected from the group consisting of SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31 and SEQ ID NO:32, and in a separate embodiment SEQ ID NO:5, SEQ ID NO:6, SEQ ID NO:7 and SEQ ID NO:8, are also embraced by the invention.

In related aspects, the invention provides an expression vector comprising the foregoing isolated nucleic acid molecules operably linked to a promoter, host cells transformed or transfected with such expression vectors, and isolated peptides encoded by the isolated nucleic acid molecules.

The invention is yet another aspect provides cell lines that produce the antibodies described herein.

These and other embodiments of the invention will be described in greater detail herein.

BRIEF DESCRIPTION OF THE SEQUENCE LISTING

Figure 1:
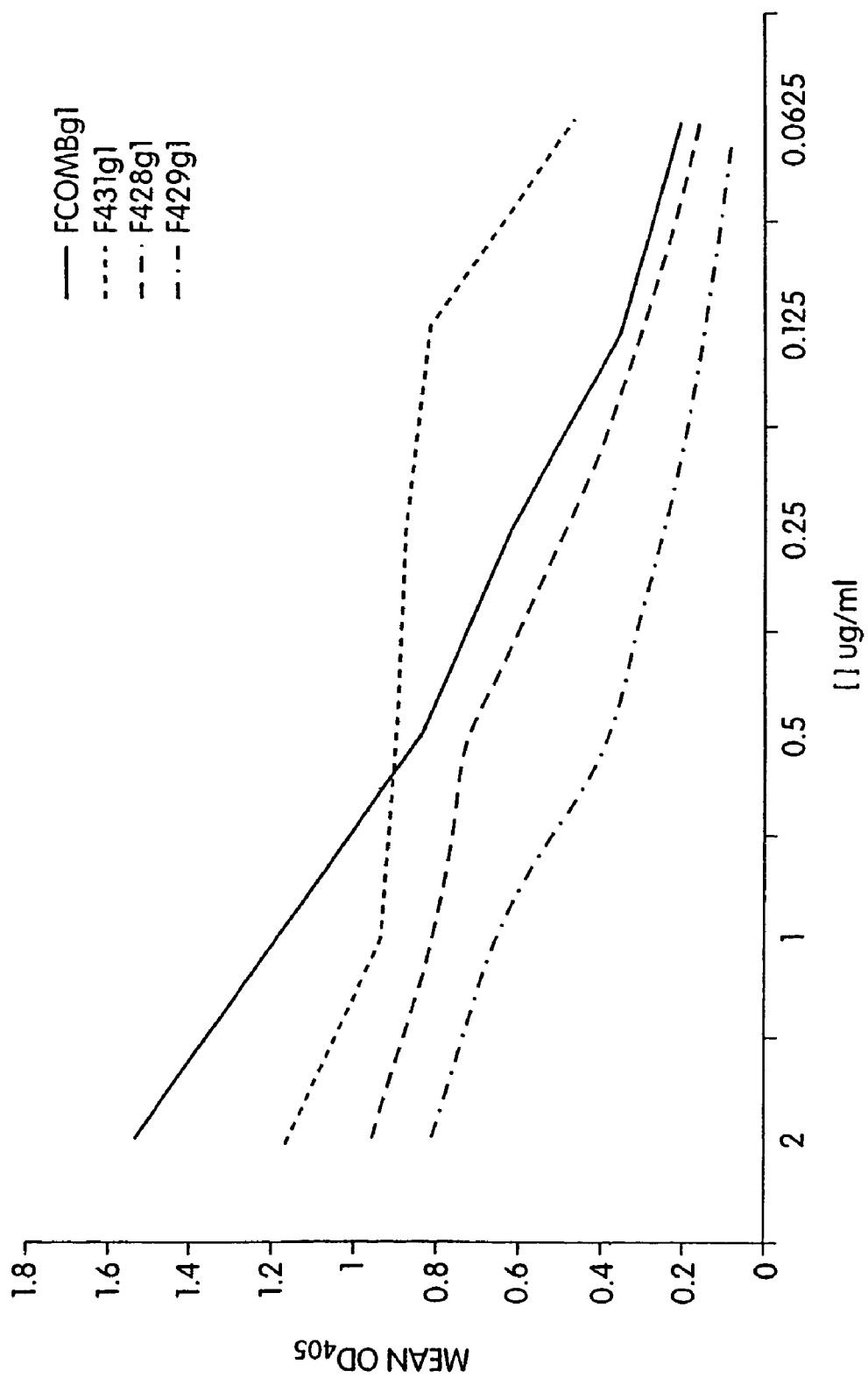
FIG. 1 is a graph showing binding of monoclonal antibodies to mucoid exopolysaccharide antigen (MEP) isolated from *P. aeruginosa* strain 2192 M in a direct ELISA as a function of antibody concentration.

SEQ ID NO:1 is the nucleotide sequence of the variable region of the heavy chain from clones F428 and F429.

SEQ ID NO:2 is the nucleotide sequence of the variable region of the light chain from clones F428 and F431.

SEQ ID NO:3 is the nucleotide sequence of the variable region of the light chain from clones F429 and COMB.

SEQ ID NO:4 is the nucleotide sequence of the variable region of the heavy chain from clones F431 and COMB.

SEQ ID NO:5 is the amino acid sequence of the variable region of the heavy chain from clones F428 and F429.

SEQ ID NO:6 is the amino acid sequence of the variable region of the light chain from clones F428 and F431.

SEQ ID NO:7 is the amino acid sequence of the variable region of the light chain from clones F429 and COMB.

SEQ ID NO:8 is the amino acid sequence of the variable region of the heavy chain from clones F431 and COMB.

SEQ ID NO:9 is the nucleotide sequence of CDR1 from SEQ ID NO:1.

SEQ ID NO:10 is the nucleotide sequence of CDR2 from SEQ ID NO:1.

SEQ ID NO: 11 is the nucleotide sequence of CDR3 from SEQ ID NO:1.

SEQ ID NO:12 is the nucleotide sequence of CDR1 from SEQ ID NO:2.

SEQ ID NO:13 is the nucleotide sequence of CDR2 from SEQ ID NO:2.

SEQ ID NO:14 is the nucleotide sequence of CDR3 from SEQ ID NO:2.

SEQ ID NO:15 is the nucleotide sequence of CDR1 from SEQ ID NO:3.

SEQ ID NO:16 is the nucleotide sequence of CDR2 from SEQ ID NO:3.

SEQ ID NO:17 is the nucleotide sequence of CDR3 from SEQ ID NO:3.

SEQ ID NO:18 is the nucleotide sequence of CDR1 from SEQ ID NO:4.

SEQ ID NO:19 is the nucleotide sequence of CDR2 from SEQ ID NO:4.

SEQ ID NO:20 is the nucleotide sequence of CDR3 from SEQ ID NO:4.

SEQ ID NO:21 is the amino acid sequence of CDR1 from SEQ ID NO:5.

SEQ ID NO:22 is the amino acid sequence of CDR2 from SEQ ID NO:5.

SEQ ID NO:23 is the amino acid sequence of CDR3 from SEQ ID NO:5.

SEQ ID NO:24 is the amino acid sequence of CDR1 from SEQ ID NO:6.

SEQ ID NO:25 is the amino acid sequence of CDR2 from SEQ ID NO:6.

SEQ ID NO:26 is the amino acid sequence of CDR3 from SEQ ID NO:6.

SEQ ID NO:27 is the amino acid sequence of CDR1 from SEQ ID NO:7.

SEQ ID NO:28 is the amino acid sequence of CDR2 from SEQ ID NO:7.

SEQ ID NO:29 is the amino acid sequence of CDR3 from SEQ ID NO:7.

SEQ ID NO:30 is the amino acid sequence of CDR1 from SEQ ID NO:8.

SEQ ID NO:31 is the amino acid sequence of CDR2 from SEQ ID NO:8.

SEQ ID NO:32 is the amino acid sequence of CDR3 from SEQ ID NO:8.

SEQ ID NO:33 is the nucleotide sequence of FR1 from SEQ ID NO:1.

SEQ ID NO:34 is the nucleotide sequence of FR2 from SEQ ID NO:1.

SEQ ID NO:35 is the nucleotide sequence of FR3 from SEQ ID NO:1.

SEQ ID NO:36 is the nucleotide sequence of FR4 from SEQ ID NO:1.

SEQ ID NO:37 is the nucleotide sequence of FR1 from SEQ ID NO:2.

SEQ ID NO:38 is the nucleotide sequence of FR2 from SEQ ID NO:2.

SEQ ID NO:39 is the nucleotide sequence of FR3 from SEQ ID NO:2.

SEQ ID NO:40 is the nucleotide sequence of FR4 from SEQ ID NO:2.

SEQ ID NO:41 is the nucleotide sequence of FR1 from SEQ ID NO:3.

SEQ ID NO:42 is the nucleotide sequence of FR2 from SEQ ID NO:3.

SEQ ID NO:43 is the nucleotide sequence of FR3 from SEQ ID NO:3.

SEQ ID NO:44 is the nucleotide sequence of FR4 from SEQ ID NO:3.

SEQ ID NO:45 is the nucleotide sequence of FR1 from SEQ ID NO:4.

SEQ ID NO:46 is the nucleotide sequence of FR2 from SEQ ID NO:4.

SEQ ID NO:47 is the nucleotide sequence of FR3 from SEQ ID NO:4.

SEQ ID NO:48 is the nucleotide sequence of FR4 from SEQ ID NO:4.

SEQ ID NO:49 is the amino acid sequence of FR1 from SEQ ID NO:5.

SEQ ID NO:50 is the amino acid sequence of FR2 from SEQ ID NO:5.

SEQ ID NO:51 is the amino acid sequence of FR3 from SEQ ID NO:5.

SEQ ID NO:52 is the amino acid sequence of FR4 from SEQ ID NO:5.

SEQ ID NO:53 is the amino acid sequence of FR1 from SEQ ID NO:6.

SEQ ID NO:54 is the amino acid sequence of FR2 from SEQ ID NO:6.

SEQ ID NO:55 is the amino acid sequence of FR3 from SEQ ID NO:6.

SEQ ID NO:56 is the amino acid sequence of FR4 from SEQ ID NO:6.

SEQ ID NO:57 is the amino acid sequence of FR1 from SEQ ID NO:7.

SEQ ID NO:58 is the amino acid sequence of FR2 from SEQ ID NO:7.

SEQ ID NO:59 is the amino acid sequence of FR3 from SEQ ID NO:7.

SEQ ID NO:60 is the amino acid sequence of FR4 from SEQ ID NO:7.

SEQ ID NO:61 is the amino acid sequence of FR1 from SEQ ID NO:8.

SEQ ID NO:62 is the amino acid sequence of FR2 from SEQ ID NO:8.

SEQ ID NO:63 is the amino acid sequence of FR3 from SEQ ID NO:8.

SEQ ID NO:64 is the amino acid sequence of FR4 from SEQ ID NO:8.

DETAILED DESCRIPTION OF THE INVENTION

The invention relates to the discovery and synthesis of peptides that bind to *P. aeruginosa* mucoid exopolysaccharide (i.e., MEP or alginate). Peptides that bind to *P. aeruginosa* MEP are referred to herein as MEP-binding peptides. These peptides preferably contain at least one *P. aeruginosa* MEP-binding complementarity determining region (CDR). As used herein, a *P. aeruginosa* MEP-binding CDR is a CDR derived from one of the antibodies recited herein, namely F428, F429, F431 or COMB. Mucoid strains of *P. aeruginosa* commonly infect subjects having cystic fibrosis. MEP is an external polysaccharide produced by mucoid strains of *P. aeruginosa* and used by such bacteria in the initial attachment to epithelia cell surfaces. MEP forms a slime-like coating around *P. aeruginosa* colonies in vivo and in vitro. It has been characterized molecularly as a polymer of uronic acids (e.g., mannuronic acid and guluronic acid). Importantly, the presence of a MEP coating around *P. aeruginosa* bacterial colonies in vivo renders these colonies partly resistant to antibiotic therapy.

Although not intending to be bound by any particular theory, it is believed that progression of chronic mucoid *P. aeruginosa* infection in cystic fibrosis patients is due to a failure to produce an adequate immune response that eliminates the pathogen. Specifically, the defect is a failure to produce opsonic antibodies specific for the MEP capsule of *P. aeruginosa*. Opsonic antibodies are antibodies that deposit themselves on an antigen or on a bacterium with and without complement and facilitate the phagocytosis of the antigen or bacterium by phagocytic cells such as antigen presenting cells (e.g., macrophages or dendritic cells). The ability to provide opsonic antibodies to the site of a *P. aeruginosa* infection should contribute to the eradication of mucoid *P. aeruginosa* from, for example, the lungs of chronically colonized cystic fibrosis patients. As used herein, the terms opsonic and opsonophagocytic are used interchangeably to refer to an antibody that is able to induce Fe mediated phagocytosis of an antigen such as a bacterium.

The invention is premised, in part, on the discovery and synthesis of human monoclonal antibodies that bind to *P. aeruginosa* MEP and enhance opsonophagocytosis of *P. aeruginosa* (i.e., opsonic human monoclonal antibodies specific for *P. aeruginosa* MEP). These antibodies were produced by molecularly manipulating antibody encoding genes from B cells harvested from human subjects immunized with purified MEP. The recombined immunoglobulin (Ig) genes from these B cells, particularly the variable region genes, were isolated from the harvested B cells and cloned into an Ig recombination vector that codes for human Ig constant region genes of both heavy and light chains. Using this technique, four novel antibodies that bind to *P. aeruginosa* MEP and enhance opsonophagocytosis of *P. aeruginosa* have been identified and synthesized. All the antibody clones are of IgG isotype and they are designated F429, F430, F431 and COMB.

The antibodies described herein are able to bind to mucoid and several non-mucoid *P. aeruginosa* strains. It is believed that strains characterized as "non-mucoid" still secrete low levels of MEP sufficient for detection by the peptides. The antibodies are capable of mediating opsonic killing of *P. aeruginosa* isolates from infected human subjects. When used in vivo in murine models of *P. aeruginosa* infection, the antibodies provide protection to *P. aeruginosa* challenge. These and other findings are described in greater detail in the Examples.

The peptides of the invention minimally comprise regions that bind to MEP (i.e., *P. aeruginosa* MEP-binding region). *P. aeruginosa* MEP-binding regions derive from the MEP-binding regions of the antibodies of the invention, or alternatively, they are functionally equivalent variants of such regions. Two particular classes of antibody derived *P. aeruginosa* MEP-binding regions are variable regions and complementarity determining regions (CDRs). Both variable regions and CDRs may easily be sequenced by one of ordinary skill in the art. A description of these regions is provided below as is the location of these regions in the antibodies and sequences of the invention.

An antibody, as is well known in the art, is an assembly of polypeptide chains linked by disulfide bridges. Two principle polypeptide chains, referred to as the light chain and heavy chain, make up all major structural classes (isotypes) of antibody. Both heavy chains and light chains are further divided into subregions referred to as variable regions and constant regions. In some instances, the peptides encompass the antibody heavy and light variable chains of the foregoing antibodies. The heavy chain variable region is a peptide which generally ranges from 100 to 150 amino acids in length. The light chain variable region is a peptide which generally ranges from 80 to 130 amino acids in length. The present invention provides four different variable regions, two of which are heavy chain variable regions and two of which are light chain variable regions. SEQ ID NO:1 and SEQ ID NO:5 correspond to the nucleotide and amino acid sequence of the heavy chain variable region derived from antibody clones F428 and F429. SEQ ID NO:2 and SEQ ID NO:6 correspond to the nucleotide and amino acid sequence of the light chain variable region derived from antibody clones F428 and F431. SEQ ID NO:3 and SEQ ID NO:7 correspond to the nucleotide and amino acid sequence of the light chain variable region derived from antibody clone F429. SEQ ID NO:4 and SEQ ID NO:8 correspond to the nucleotide and amino acid sequence of the heavy chain variable region derived from antibody clone F431.

Alternatively, the peptides encompass only the complementarity determining regions (i.e., CDRs) of the foregoing variable regions. As is well-known in the art, CDRs of an antibody are the portions of the antibody which are largely responsible for antibody specificity. The CDRs directly interact with the epitope of the antigen (see, in general, Clark, 1986; Roitt, 1991). In both the heavy chain and the light chain variable regions of IgG immunoglobulins, there are four framework regions (FR1 through FR4) separated respectively by three complementarity determining regions (CDR1, CDR 2 and CDR3). The framework regions (FRs) maintain the tertiary structure of the paratope, which is the portion of the antibody which is involved in the interaction with the antigen. CDRs, and in particular CDR3, and more particularly heavy chain CDR3, contribute to antibody specificity. Because CDRs, and in particular CDR3, confer antigen specificity on the antibody, these regions may be incorporated into other antibodies or peptides to confer the identical antigen specificity onto that antibody or peptide.

The *P. aeruginosa* MEP-binding region may be a *P. aeruginosa* MEP-binding CDR1, a *P. aeruginosa* MEP-binding CDR2, or a *P. aeruginosa* MEP-binding CDR3, all of which are derived from the antibodies and antibody variable chains disclosed herein. As used herein, a "*P. aeruginosa* MEP-binding CDR1" is a CDR1 that binds, preferably specifically, to *P. aeruginosa* MEP, and is derived from either the heavy or light chain variable regions of the antibodies described herein. It preferably has an amino acid sequence selected from the group consisting of SEQ ID NO:21, SEQ ID NO:24, SEQ ID NO:27 and SEQ ID NO:30. Similar respective definitions apply to *P. aeruginosa* binding CDR2 and CDR3. A "*P. aeruginosa* MEP-binding CDR2" is a CDR2 that binds, preferably specifically, to *P. aeruginosa* MEP, and is derived from either the heavy or light chain variable regions of the antibodies described herein. It has an amino acid sequence selected from the group consisting of SEQ ID NO:22, SEQ ID NO:25, SEQ ID NO:28 and SEQ ID NO:31. A "*P. aeruginosa* MEP-binding CDR3" is a CDR3 that binds, preferably specifically, to *P. aeruginosa* MEP, and is derived from either the heavy or light chain variable regions of the antibodies described herein. It preferably has an amino acid sequence selected from the group consisting of SEQ ID NO:23, SEQ ID NO:26, SEQ ID NO:29 and SEQ ID NO:32. In addition to the sequences listed above, the invention intends to embrace functionally equivalent variants of these sequences including conservative substitution variants, as described in greater detail below.

The peptides of the invention, including but not limited to the opsonophagocytic antibodies discussed herein, are useful inter alia in diagnostic methods aimed at detecting *P. aeruginosa* bacteria in a sample in or from a subject. At a minimum, peptides useful in these methods need only recognize and bind to *P. aeruginosa* MEP, regardless of whether they also enhance opsonization and phagocytosis. In important embodiments, the antibodies and fragments thereof bind to MEP selectively. Accordingly, they need only possess one or more of the CDRs derived from the antibody clones described herein. In preferred embodiment, the peptides comprise a MEP-binding CDR3, and even more preferably, the peptides comprise a heavy chain MEP-binding CDR3. It is to be understood that not all of the CDRs are required in order to effect binding to P. aeruginosa MEP. However, in some embodiments the peptides comprise all of the CDRs disclosed herein.

In addition, it should be understood that the invention also embraces the exchange of CDRs between the variable regions provided herein. Preferably, a heavy chain CDR is exchanged with another heavy chain variable region CDR, and likewise, a light chain CDR is exchanged with another light chain variable region CDR.

The nucleotide sequences of the CDRs of the variable chains disclosed in the present invention are as follows:

| Clone | Chain | CDR  | SEQ ID NO: | Sequence |
|-------|-------|------|------------|----------|
| F428  | Hv    | CDR1 | 9          | TAT ATT AAT TAC TAC TGG GGC |
| F428  | Hv    | CDR2 | 10         | AGT ATC CAT TAT GAT GGG AGC ACC TTC TAC AAC CCG TCC CTC AAG AGT |
| F428  | Hv    | CDR3 | 11         | ACG TAT TAC GAT GCT TCG GGG AGC CCT TAC TTT GAC CAC |
| F428  | Lt    | CDR1 | 12         | TCT GGA AGC AGC TCC AAC CTT GGG AAC AAT TTT GTA TCC |
| F428  | Lt    | CDR2 | 13         | GAC AAT GAT AAG CGA CCC TCA |
| F428  | Lt    | CDR3 | 14         | GGA ACA TGG GAT AGC AGC CTG ACT GCT TAT GTC |
| F429  | Lt    | CDR1 | 15         | TCT GGA AGC AGC TCC AAC ATT GGG AAT AAT TAT GTA TCC |
| F429  | Lt    | CDR2 | 16         | GAC AAT AAT AAG CGA CCC TCA |
| F429  | Lt    | CDR3 | 17         | GGA ACA TGG GAT AGC AGC CTG AGT ACT TGG GTG |
| F431  | Hv    | CDR1 | 18         | AGT AAT AAT TAC TAC TGG GGC |
| F431  | Hv    | CDR2 | 19         | ACT ATC TCT TAT AAT GGG TAC ACC TAC TAC ATC CCG TCC CTC AGG GGT |
| F431  | Hv    | CDR3 | 20         | CAT GAC TAT AGC ATG TCG TCC GGA CTT ACT GAC AAC TGG TTC GAC CCC |

The amino acid sequences of the CDRs of the variable chains disclosed in the present invention are as follows:

| Clone | Chain | CDR  | SEQ ID NO: | Sequence |
|-------|-------|------|------------|----------|
| F428  | Hv    | CDR1 | 21         | YINYYWG |
| F428  | Hv    | CDR2 | 22         | SIHYDGSTFYNPSLKS |
| F428  | Hv    | CDR3 | 23         | TYYDASGSPYFDH |
| F428  | Lt    | CDR1 | 24         | SGSSSNLGNNFVS |
| F428  | Lt    | CDR2 | 25         | DNDKRPS |
| F428  | Lt    | CDR3 | 26         | GTWDSSLTAYV |
| F429  | Lt    | CDR1 | 27         | SGSSSNIGNNYVS |
| F429  | Lt    | CDR2 | 28         | DNNKRPS |
| F429  | Lt    | CDR3 | 29         | GTWDSSLSTWV |
| F431  | Hv    | CDR1 | 30         | SNNYYWG |
| F431  | Hv    | CDR2 | 31         | TISYNGYTYYIPSLRG |
| F431  | Hv    | CDR3 | 32         | HDYSMSSGLTDNWFDP |

As used herein, the term "peptide" includes monoclonal antibodies, functionally active and/or equivalent antibody fragments, and functionally active and/or equivalent peptides and polypeptides. The peptides of the invention are isolated peptides. As used herein, the term "isolated peptides" means that the peptides are substantially pure and are essentially free of other substances with which they may be found in nature or in vivo systems to an extent practical and appropriate for their intended use. In particular, the peptides are sufficiently pure and are sufficiently free from other biological constituents of their hosts cells so as to be useful in, for example, producing pharmaceutical preparations or sequencing. Because an isolated peptide of the invention may be admixed with a pharmaceutically acceptable carrier in a pharmaceutical preparation, the peptide may comprise only a small percentage by weight of the preparation. The peptide is nonetheless substantially pure in that it has been substantially separated from the substances with which it may be associated in living systems.

The peptides of the invention bind to MEP, preferably in a selective manner. As used herein, the terms "selective binding" and "specific binding" are used interchangeably to refer to the ability of the peptide to bind with greater affinity to MEP and fragments thereof than to non-MEP derived compounds. That is, peptides that bind selectively to MEP will not bind to non-MEP derived compounds to the same extent and with the same affinity as they bind to MEP and fragments thereof. In preferred embodiments, the peptides of the invention bind solely to MEP and fragments thereof.

As stated earlier, the invention provides peptides e.g., antibodies or antibody fragments, that bind to P. aeruginosa MEP. Such antibodies preferably enhance opsonization and phagocytosis (i.e., opsonophagocytosis) of P. aeruginosa, and as a result are useful in the prevention and therapy of a P. aeruginosa infection in a subject. Opsonization refers to a process by which phagocytosis is facilitated by the deposition of opsonins (e.g., antibody or complement factor C3b) on the antigen. Phagocytosis refers to the process by which phagocytic cells (e.g., macrophages, dendritic cells, and polymorphonuclear leukocytes (PMNL)) engulf material and enclose it within a vacuole (e.g., a phagosome) in their cytoplasm. Thus, antibodies or antibody fragments that enhance opsonization and phagocytosis are antibodies or antibody fragments that recognize and deposit onto an antigen, and in doing so, facilitate the uptake and engulfment of the antigen (and the antigen-bearing substance, e.g., P. aeruginosa bacteria) by phagocytic cells. Generally, in order to enhance phagocytosis and opsonization, the antibody comprises an Fc domain or region. The Fc domain is recognized by Fc receptor bearing cells (e.g., antigen presenting cells such as macrophages, or PMNL). As used herein, "to enhance opsonophagocytosis" means to increase the likelihood that an antigen or an antigen bearing substrate will be recognized and engulfed by a phagocytic cell, via antibody deposition. This enhancement can be measured by reduction in bacterial load in vivo or by bacterial cell killing in vitro using the in vitro methods described below.

Opsonization assays are standard in the art. Generally such assays measure the amount of bacterial killing in the presence of an antibody, an antigen (expressed on the target bacterial cell), complement, and phagocytic cells. Serum is commonly used as a source of complement, and polymorphonuclear cells are commonly used as a source of phagocytic cells. The target cell source can be prokaryotic (as in the present invention) or eukaryotic, depending upon which cell type expresses the antigen. Cell killing can be measured by viable cell counts prior to and following incubation of the reaction components. Alternatively, cell killing can be quantitated by measuring labeled cell contents in the supernatant of the reaction mixture (i.e., chromium release). Other assays will be apparent to those of skill in the art, having read the present specification, which are useful for determining whether an antibody or antibody fragment that binds to P. aeruginosa MEP also stimulates opsonization and phagocytosis.

The present invention provides, inter alia, MEP-specific human monoclonal antibodies that enhance opsonic killing of mucoid P. aeruginosa. These antibodies are named F428, F429, F431 and COMB. When used in vivo, human monoclonal antibodies are far less likely to be immunogenic (as compared to antibodies from another species). As a result, these antibodies represent novel agents useful in the design of vaccines as well as passive immunotherapy targeting P. aeruginosa. The synthesis of these monoclonal antibodies is described in the Examples. Briefly, the antibodies were derived from B cells harvested from individuals immunized with MEP as described in U.S. Pat. No. 4,578,458. Harvested B cells were transformed using Epstein-Barr virus, and then fused with an immortalized cell line fusion partner called HMMA 2.5. Single antibody producing clones were grown and analyzed separately using a binding assay (e.g., ELISA). Three antibodies were selected based on their ability to bind to P. aeruginosa MEP. All three antibodies were of IgA isotype. cDNA coding for the heavy and light variable regions of the three antibodies was then isolated and sequenced. Variable region cDNA was cloned into an human Ig expression vector (i.e., TCAE 5.3) that contained Ig constant region coding sequences for both heavy and light chains. These expression vectors were then transfected into cells (e.g., CHO DG44 cells), the cells were grown in vitro, and Ig was subsequently harvested from the supernatant. Resultant antibodies possessed human variable regions and human IgG constant regions. Their ability to bind to P. aeruginosa, specifically to P. aeruginosa MEP, and to enhance opsonization and phagocytosis of P. aeruginosa was evaluated using binding and opsonophagocytic killing assays such as those described herein.

Thus in one embodiment, the peptide of the invention is an isolated intact soluble monoclonal antibody specific for P. aeruginosa MEP. As used herein, the term "monoclonal antibody" refers to a homogenous population of immunoglobulins that specifically bind to an identical epitope (i.e., antigenic determinant). The peptide of the invention in one embodiment is, for example, a monoclonal antibody having a heavy chain variable region having an amino acid sequence of SEQ ID NO:5. In another embodiment, the monoclonal antibody has a heavy chain variable region having an amino acid sequence of SEQ ID NO:8. The monoclonal antibody can have a light chain variable region having an amino acid sequence of SEQ ID NO:6 or SEQ ID NO:7. Monoclonal antibodies having any combination of light chain and heavy chain variable regions are embraced by the invention. Using the nomenclature set forth in the Examples for denoting heavy and light chain variable regions and their corresponding amino acid and nucleic acid sequences, the following combinations can be included in a monoclonal antibody of the invention: heavy chain A (SEQ ID NO:5) and light chain 1 (SEQ ID NO:6); heavy chain A (SEQ ID NO:5) and light chain 2 (SEQ ID NO:7); heavy chain B (SEQ ID NO:8) and light chain 1 (SEQ ID NO:6); and heavy chain B (SEQ ID NO:8) and light chain 2 (SEQ ID NO:7).

The invention intends to encompass antibodies other than for example clones F428, F429, F431 and COMB, provided that such antibodies have the binding characteristics of the monoclonal antibodies described herein. Optionally, these additional antibodies also enhance opsonophagocytosis of P. aeruginosa cells. One of ordinary skill in the art can easily identify antibodies having the functional characteristics (e.g., binding, opsonizing and phagocytosing attributes) of these monoclonal antibody using the screening and binding assays set forth in detail herein.

In other embodiments, the peptide is an antibody fragment. As is well-known in the art, only a small portion of an antibody molecule, the paratope, is involved in the binding of the antibody to its epitope (see, in general, Clark, W. R. (1986) *The Experimental Foundations of Modern Immunology* Wiley & Sons, Inc., New York; Roitt, I. (1991) *Essential Immunology*, 7th Ed., Blackwell Scientific Publications, Oxford). The pFc' and Fc regions of the antibody, for example, are effectors of the complement cascade but are not involved in antigen binding. An antibody from which the pFc' region has been enzymatically cleaved, or which has been produced without the pFc' region, designated an F(ab')₂ fragment, retains both of the antigen binding sites of an intact antibody. An isolated F(ab')₂ fragment is referred to as a bivalent monoclonal fragment because of its two antigen binding sites. Similarly, an antibody from which the Fe region has been enzymatically cleaved, or which has been produced without the Fe region, designated an Fab fragment, retains one of the antigen binding sites of an intact antibody molecule. Proceeding further, Fab fragments consist of a covalently bound antibody light chain and a portion of the antibody heavy chain denoted Fd (heavy chain variable region). The Fd fragments are the major determinant of antibody specificity (a single Fd fragment may be associated with up to ten different light chains without altering antibody specificity) and Fd fragments retain epitope-binding ability in isolation.

The terms Fab, Fc, pFc', F(ab')₂ and Fv are employed with either standard immunological meanings [Klein, Immunology (John Wiley, New York, N.Y., 1982); Clark, W. R. (1986) The Experimental Foundations of Modern Immunology (Wiley & Sons, Inc., New York); Roitt, I. (1991) Essential Immunology, 7th Ed., (Blackwell Scientific Publications, Oxford)].

In other embodiments, the Fc portions of the antibodies of the invention may be replaced so as to produce IgM as well as human IgG antibodies bearing some or all of the CDRs of the monoclonal antibodies described herein. Of particular importance is the inclusion of a P. aeruginosa MEP-binding CDR3 region and, to a lesser extent, the other CDRs and portions of the framework regions of the monoclonal antibodies described herein. Such human antibodies will have particular clinical utility in that they will recognize and bind, preferably selectively, to P. aeruginosa MEP, but will not evoke an immune response in humans against the antibody itself.

The invention also intends to include functionally equivalent variants of the P. aeruginosa MEP-binding peptides. A "functionally equivalent variant" is a compound having the same function (i.e., the ability to bind to P. aeruginosa MEP and in some embodiments to facilitate opsonization of the bacterium) as the peptides of the invention. A functionally equivalent variant may be peptide in nature but it is not so limited. For example, it may be a carbohydrate, a peptidomimetic, etc. In important embodiments, the functionally equivalent variant is a peptide having the amino acid sequence of a variable region or a CDR with conservative substitutions therein, that is still capable of binding to P. aeruginosa MEP. An example of a functionally equivalent variant of P. aeruginosa MEP-binding CDR3 from the heavy chain variable region of clone F428 (i.e., SEQ ID NO:5) is a peptide having conservative substitutions in SEQ ID NO:5 which bind, preferably specifically, to P. aeruginosa MEP, and optionally which enhances opsonization of P. aeruginosa. As used herein, "conservative substitution" refers to an amino acid substitution which does not alter the relative charge or size characteristics of the peptide in which the amino acid substitution is made. Conservative substitutions of amino acids include substitutions made amongst amino acids with the following groups: (1) M,I,L,V; (2) F,Y,W; (3) K,R,H; (4) A,G; (5) S,T; (6) Q,N; and, (7) E,D.

Functional equivalent variants can have identity to the peptides explicitly recited herein. That is, such variants may have at least 99% identity, at least 98% identity, at least 97% identity, at least 96% identity, at least 95% identity, at least 94% identity, at least 93% identity, at least 92% identity, at least 91% identity, at least 90% identity, at least 85% identity, at least 80% identity, at least 75% identity, at least 70% identity, at least 65% identity, at least 60% identity, at least 55% identity, at least 50% identity, at least 45% identity, at least 40% identity, at least 35% identity, at least 30% identity, at least 25% identity, at least 20% identity, at least 10% identity, or at least 5% identity to the amino acid sequences provided herein.

Functional equivalence refers to an equivalent activity (e.g., binding to P. aeruginosa MEP, or enhancing opsonophagocytosis of P. aeruginosa), however it also embraces variation in the level of such activity. For example, a functional equivalent is a variant that binds to P. aeruginosa MEP with lesser, equal, or greater affinity than the monoclonal antibody clones described herein, provided that the variant is still useful in the invention (i.e., it binds to P. aeruginosa MEP and optionally enhances opsonophagocytosis of P. aeruginosa).

Such substitutions can be made by a variety of methods known to one of ordinary skill in the art. For example, amino acid substitutions may be made by PCR-directed mutation, site-directed mutagenesis according to the method of Kunkel (Kunkel, Proc. Nat. Acad. Sci. U.S.A. 82: 488–492, 1985), or by chemical synthesis of a gene encoding the particular CDR. These and other methods for altering a CDR containing peptide will be known to those of ordinary skill in the art and may be found in references which compile such methods, e.g. Sambrook or Ausubel, noted above. In some embodiments, however, due to the size of the CDRs, it may be more convenient to synthesize the variant peptides using a peptide synthesizer such as those commercially available. The activity of functionally equivalent variants of the P. aeruginosa MEP-binding CDR can be tested by the binding assays, and in some cases biological activity assays, as discussed in more detail below. As used herein, the terms "functional variant", "functionally equivalent variant" and "functionally active variant" are used interchangeably.

As used herein the term "functionally active antibody fragment" means a fragment of an antibody molecule including a P. aeruginosa MEP-binding region of the invention which retains the ability to bind to P. aeruginosa MEP, preferably in a specific manner. Such fragments can be used both in vitro and in vivo. In particular, well-known functionally active antibody fragments include but are not limited to F(ab')₂, Fab, Fv and Fd fragments of antibodies. These fragments which lack the Fe fragment of intact antibody, clear more rapidly from the circulation, and may have less non-specific tissue binding than an intact antibody (Wahl et al., J. Nucl. Med. 24:316–325 (1983)). As another example, single-chain antibodies can be constructed in accordance with the methods described in U.S. Pat. No. 4,946,778 to Ladner et al. Such single-chain antibodies include the variable regions of the light and heavy chains joined by a flexible linker moiety. Methods for obtaining a single domain antibody ("Fd") which comprises an isolated variable heavy chain single domain, also have been reported (see, for example, Ward et al., Nature 341:644–646 (1989), disclosing a method of screening to identify an antibody heavy chain variable region ($V_H$ single domain antibody) with sufficient affinity for its target epitope to bind thereto in isolated form). Methods for making recombinant Fv fragments based on known antibody heavy chain and light chain variable region sequences are known in the art and have been described, e.g., Moore et al., U.S. Pat. No. 4,462,334. Other references describing the use and generation of antibody fragments include e.g., Fab fragments (Tijssen, Practice and Theory of Enzyme Immunoassays (Elsevier, Amsterdam, 1985)), Fv fragments (Hochman et al., Biochemistry 12: 1130 (1973); Sharon et al., Biochemistry 15:

1591 (1976); Ehrlich et al., U.S. Pat. No. 4,355,023) and portions of antibody molecules (Audilore-Hargreaves, U.S. Pat. No. 4,470,925). Thus, those skilled in the art may construct antibody fragments from various portions of intact antibodies without destroying the specificity of the antibodies for the *P. aeruginosa* MEP epitope.

In important aspects of the invention, the functionally active antibody fragment also retains the ability to opsonize and phagocytose *P. aeruginosa*. In this latter instance, the antibody fragment includes an Fc region as well as an epitope binding domain. The Fc region allows the antibody fragment to bind to Fc receptor positive cells, which subsequently phagocytose the epitope bound by the Fab region of the antibody.

Still other screening assays for identifying peptides of the invention are performed for example, using phage display procedures such as those described in Hart, et al., *J. Biol. Chem.* 269:12468 (1994). Hart et al. report a filamentous phage display library for identifying novel peptide ligands for mammalian cell receptors. In general, phage display libraries using, e.g., M13 or fd phage, are prepared using conventional procedures such as those described in the foregoing reference. The libraries display inserts containing from 4 to 80 amino acid residues. The inserts optionally represent a completely degenerate or a biased array of peptides. Ligands that bind, preferably selectively, to *P. aeruginosa* MEP are obtained by selecting those phages which express on their surface a ligand that binds to *P. aeruginosa* MEP. These phages then are subjected to several cycles of reselection to identify the peptide ligand-expressing phages that have the most useful binding characteristics. Typically, phages that exhibit the best binding characteristics (e.g., highest affinity) are further characterized by nucleic acid analysis to identify the particular amino acid sequences of the peptides expressed on the phage surface and the optimum length of the expressed peptide to achieve optimum binding to *P. aeruginosa* MEP. Alternatively, such peptide ligands can be selected from combinatorial libraries of peptides containing one or more amino acids. Such libraries can further be synthesized which contain non-peptide synthetic moieties which are less subject to enzymatic degradation compared to their naturally-occurring counterparts.

Additionally small peptides including those containing the *P. aeruginosa* MEP-binding CDR3 region may easily be synthesized or produced by recombinant means to produce the peptide of the invention. Such methods are well known to those of ordinary skill in the art. Peptides can be synthesized for example, using automated peptide synthesizers which are commercially available. The peptides can be produced by recombinant techniques by incorporating the DNA expressing the peptide into an expression vector and transforming cells with the expression vector to produce the peptide.

Peptides, including antibodies, can be tested for their ability to bind to *P. aeruginosa* MEP using standard binding assays known in the art. As an example of a suitable assay, *P. aeruginosa* MEP can be immobilized on a surface (such as in a well of a multi-well plate) and then contacted with a labeled peptide. The amount of peptide that binds to the *P. aeruginosa* MEP (and thus becomes itself immobilized onto the surface) may then be quantitated to determine whether a particular peptide binds to *P. aeruginosa* MEP. Alternatively, the amount of peptide not bound to the surface may also be measured. In a variation of this assay, the peptide can be tested for its ability to bind directly to a *P. aeruginosa* colony grown in vitro. An example of this latter assay is described in greater detail in the Examples.

Peptide binding can also be tested using a competition assay. If the peptide being tested competes with the monoclonal antibodies or antibody fragments described herein, as shown by a decrease in binding of the monoclonal antibody or fragment, then it is likely that the peptide and the monoclonal antibody bind to the same, or at least an overlapping, epitope. In this assay system, the antibody or antibody fragment is labeled and the *P. aeruginosa* MEP is immobilized onto the solid surface. These and other assays are described in more detail herein.

Standard binding assays are well known in the art, and a number of these are suitable in the present invention including ELISA, competition binding assay (as described above), sandwich assays, radioreceptor assays using radioactively labeled peptides or radiolabeled antibodies, immunoassays, etc. The nature of the assay is not essential provided it is sufficiently sensitive to detect binding of a small number of peptides.

A variety of other reagents also can be included in the binding mixture. These include reagents such as salts, buffers, neutral proteins (e.g., albumin), detergents, etc. which may be used to facilitate optimal binding. Such a reagent may also reduce non-specific or background interactions of the reaction components. Other reagents that improve the efficiency of the assay may also be used. The mixture of the foregoing assay materials is incubated under conditions under which the monoclonal antibody normally specifically binds *P. aeruginosa* MEP. Such conditions will preferably mimic physiological conditions. The order of addition of components, incubation temperature, time of incubation, and other parameters of the assay may be readily determined. Such experimentation merely involves optimization of the assay parameters, not the fundamental composition of the assay. Incubation temperatures typically are between 4° C. and 40° C. Incubation times preferably are minimized to facilitate rapid, high throughput screening, and typically are between 0.1 and 10 hours. After incubation, the presence or absence of specific binding between the peptide and *P. aeruginosa* MEP is detected by any convenient method available to the user.

Typically, a plurality of assay mixtures are run in parallel with different peptides or different peptide concentrations to obtain a different response to the various concentrations. One of these concentrations serves as a negative control, i.e., at zero concentration of *P. aeruginosa* MEP or at a concentration of *P. aeruginosa* MEP below the limits of assay detection.

A separation step is often used to separate bound from unbound peptide or antibody. The separation step may be accomplished in a variety of ways. Conveniently, at least one of the components (e.g., peptide or antibody) is immobilized on a solid substrate via binding to *P. aeruginosa* MEP. The unbound components may be easily separated from the bound fraction. The solid substrate can be made of a wide variety of materials and in a wide variety of shapes, e.g., columns or gels of polyacrylamide, agarose or sepharose, microtiter plates, microbeads, resin particles, etc. The separation step preferably includes multiple rinses or washes. For example, when the solid substrate is a microtiter plate, the wells may be washed several times with a washing solution, which typically includes those components of the incubation mixture that do not participate in specific bindings such as salts, buffer, detergent, non-specific protein, etc.

Where the solid substrate is a magnetic bead, the beads may be washed one or more times with a washing solution and isolated using a magnet.

The peptides can be used alone or in conjugates with other molecules such as detection or cytotoxic agents in the detection and treatment methods of the invention, as described in more detail herein.

Typically, one of the components usually comprises, or is coupled or conjugated to a detectable label. A detectable label is a moiety, the presence of which can be ascertained directly or indirectly. Generally, detection of the label involves an emission of energy by the label. The label can be detected directly by its ability to emit and/or absorb light of a particular wavelength (e.g., radioactivity, luminescence, optical or electron density, etc.). A label can be detected indirectly by its ability to bind, recruit and, in some cases, cleave another moiety which itself may emit or absorb light of a particular wavelength (e.g., epitope tag such as the FLAG epitope, enzyme tag such as horseradish peroxidase, etc.). An example of indirect detection is the use of a first enzyme label which cleaves a substrate into visible products. The label may be of a chemical, peptide or nucleic acid molecule nature although it is not so limited. Other detectable labels include radioactive isotopes such as $P^{32}$ or $H^3$, luminescent markers such as fluorochromes, optical or electron density markers, etc., or epitope tags such as the FLAG epitope or the HA epitope, biotin, avidin, and enzyme tags such as horseradish peroxidase, β-galactosidase, etc. The label may be bound to a peptide during or following its synthesis. There are many different labels and methods of labeling known to those of ordinary skill in the art. Examples of the types of labels that can be used in the present invention include enzymes, radioisotopes, fluorescent compounds, colloidal metals, chemiluminescent compounds, and bioluminescent compounds. Those of ordinary skill in the art will know of other suitable labels for the peptides described herein, or will be able to ascertain such, using routine experimentation. Furthermore, the coupling or conjugation of these labels to the peptides of the invention can be performed using standard techniques common to those of ordinary skill in the art.

Another labeling technique which may result in greater sensitivity consists of coupling the peptides to low molecular weight haptens. These haptens can then be specifically altered by means of a second reaction. For example, it is common to use haptens such as biotin, which reacts with avidin, or dinitrophenol, pyridoxal, or fluorescein, which can react with specific anti-hapten antibodies.

Conjugation of the peptides including antibodies or fragments thereof to a detectable label facilitates, among other things, the use of such agents in diagnostic assays. Another category of detectable labels includes diagnostic and imaging labels such as for magnetic resonance imaging (MRI): Gd(DOTA); for nuclear medicine: $^{201}$Tl, gamma-emitting radionuclide 99mTc; for positron-emission tomography (PET): positron-emitting isotopes, (18)F-fluorodeoxyglucose ((18)FDG), (18)F-fluoride, copper-64, gadodiamide, and radioisotopes of Pb(II) such as 203Pb; 111In.

The conjugations or modifications described herein employ routine chemistry, which chemistry does not form a part of the invention and which chemistry is well known to those skilled in the art of chemistry. The use of protecting groups and known linkers such as mono- and hetero-bifunctional linkers are well documented in the literature and will not be repeated here.

As used herein, "conjugated" means two entities stably bound to one another by any physiochemical means. It is important that the nature of the attachment is such that it does not impair substantially the effectiveness of either entity. Keeping these parameters in mind, any covalent or non-covalent linkage known to those of ordinary skill in the art may be employed. In some embodiments, covalent linkage is preferred. Noncovalent conjugation includes hydrophobic interactions, ionic interactions, high affinity interactions such as biotin-avidin and biotin-streptavidin complexation and other affinity interactions. Such means and methods of attachment are well known to those of ordinary skill in the art.

A variety of methods may be used to detect the label, depending on the nature of the label and other assay components. For example, the label may be detected while bound to the solid substrate or subsequent to separation from the solid substrate. Labels may be directly detected through optical or electron density, radioactive emissions, nonradiative energy transfers, etc. or indirectly detected with antibody conjugates, streptavidin-biotin conjugates, etc. Methods for detecting the labels are well known in the art.

The monoclonal antibodies described herein can also be used to produce anti-idiotypic antibodies that can be used to screen and identify other antibodies having the same binding specificity as the monoclonal antibodies of the invention. An anti-idiotypic antibody is an antibody which recognizes unique determinants present on a monoclonal antibody of the invention. These determinants are located in the hypervariable region of the antibody. It is this region that binds to a given epitope and is thereby responsible for the specificity of the antibody. Such anti-idiotypic antibodies can be produced using well-known hybridoma techniques (Kohler and Milstein, *Nature,* 256:495, 1975). As an example, an anti-idiotypic antibody can be prepared by immunizing a subject with the monoclonal antibody. The immunized subject will recognize and respond to the idiotypic determinants of the immunizing monoclonal antibody and produce an antibody to these idiotypic determinants. By using the anti-idiotypic antibodies of the immunized animal, which are specific for the monoclonal antibody of the invention, it is possible to identify other clones with the same idiotype as the monoclonal antibody used for immunization. Idiotypic identity between monoclonal antibodies of two cell lines demonstrates that the two monoclonal antibodies are the same with respect to their recognition of the same epitopic determinant. Thus, by using anti-idiotypic antibodies, it is possible to identify other hybridomas expressing monoclonal antibodies having the same epitopic specificity.

The anti-idiotypic antibodies can also be used for active immunization (Herlyn, et al., Science, 232:100, 1986), since it is possible to use the anti-idiotype technology to produce monoclonal antibodies that mimic an epitope. For example, an anti-idiotypic monoclonal antibody made to a first monoclonal antibody will have a binding domain in the hypervariable region which is the image of the epitope bound by the first monoclonal antibody. Thus, the anti-idiotypic monoclonal antibody can be used for immunization, since the anti-idiotype monoclonal antibody binding domain effectively acts as an antigen.

The sequences responsible for the specificity of the monoclonal antibodies of the invention have been determined. Accordingly, peptides according to the invention can be prepared using recombinant DNA technology. There are entities in the United States which will perform this function commercially, such as Thomas Jefferson University and the Scripps Protein and Nucleic Acids Core Sequencing Facility (La Jolla, Calif.). For example, the variable region cDNA can be prepared by polymerase chain reaction from the deposited hybridoma RNA using degenerate or non-degenerate primers (derived from the amino acid sequence). The cDNA can be subcloned to produce sufficient quantities of double stranded DNA for sequencing by conventional sequencing reactions or equipment.

With knowledge of the nucleic acid sequences of the heavy chain and light chain variable domains of the *P. aeruginosa* MEP monoclonal antibody, one of ordinary skill in the art is able to produce nucleic acids which encode this antibody or which encode the various antibody fragments, humanized antibodies, or polypeptides described above. It is contemplated that such nucleic acids will be operably joined to other nucleic acids forming a recombinant vector for cloning or for expression of the peptides of the invention. The present invention includes any recombinant vector containing the coding sequences, or part thereof, whether for prokaryotic or eukaryotic transformation, transfection or gene therapy. Such vectors may be prepared using conventional molecular biology techniques, known to those with skill in the art, and would comprise DNA coding sequences for the CDR region (and preferably the CDR3 region) and additional variable sequences contributing to the specificity of the antibodies or parts thereof, as well as other non-specific peptide sequences and a suitable promoter either with (Whittle et al., *Protein Eng.* 1:499, 1987 and Burton et al., *Science* 266:1024–1027, 1994) or without (Marasco et al., *Proc. Natl. Acad. Sci. (USA)* 90:7889, 1993 and Duan et al., *Proc. Natl. Acad. Sci. (USA)* 91:5075–5079, 1994) a signal sequence for export or secretion. Such vectors may be transformed or transfected into prokaryotic (Huse et al., *Science* 246:1275, 1989, Ward et al., *Nature* 341: 644–646, 1989; Marks et al., *J. Mol. Biol.* 222:581, 1991 and Barbas et al., *Proc. Natl. Acad. Sci. (USA)* 88:7978, 991) or eukaryotic (Whittle et al., 1987 and Burton et al., 1994) cells or used for gene therapy (Marasco et al., 1993 and Duan et al., 1994) by conventional techniques, known to those with skill in the art.

As used herein, a "vector" may be any of a number of nucleic acids into which a desired sequence may be inserted by restriction and ligation for transport between different genetic environments or for expression in a host cell. Vectors are typically composed of DNA although RNA vectors are also available. Vectors include, but are not limited to, plasmids and phagemids. A cloning vector is one which is able to replicate in a host cell, and which is further characterized by one or more endonuclease restriction sites at which the vector may be cut in a determinable fashion and into which a desired DNA sequence may be ligated such that the new recombinant vector retains its ability to replicate in the host cell. In the case of plasmids, replication of the desired sequence may occur many times as the plasmid increases in copy number within the host bacterium or just a single time per host before the host reproduces by mitosis. In the case of phage, replication may occur actively during a lytic phase or passively during a lysogenic phase. An expression vector is one into which a desired DNA sequence may be inserted by restriction and ligation such that it is operably joined to regulatory sequences and may be expressed as an RNA transcript. Vectors may further contain one or more marker sequences suitable for use in the identification of cells which have or have not been transformed or transfected with the vector. Markers include, for example, genes encoding proteins which increase or decrease either resistance or sensitivity to antibiotics or other compounds, genes which encode enzymes whose activities are detectable by standard assays known in the art (e.g., β-galactosidase or alkaline phosphatase), and genes which visibly affect the phenotype of transformed or transfected cells, hosts, colonies or plaques. Preferred vectors are those capable of autonomous replication and expression of the structural gene products present in the DNA segments to which they are operably joined.

The expression vectors of the present invention include regulatory sequences operably joined to a nucleotide sequence encoding one of the peptides of the invention. As used herein, the term "regulatory sequences" means nucleotide sequences which are necessary for, or conducive to, the transcription of a nucleotide sequence which encodes a desired polypeptide and/or which are necessary for or conducive to the translation of the resulting transcript into the desired polypeptide. Regulatory sequences include, but are not limited to, 5' sequences such as operators, promoters and ribosome binding sequences, and 3' sequences such as polyadenylation signals. The vectors of the invention may optionally include 5' leader or signal sequences, 5' or 3' sequences encoding fusion products to aid in protein purification, and various markers which aid in the identification or selection of transformants. The choice and design of an appropriate vector is within the ability and discretion of one of ordinary skill in the art. The subsequent purification of the peptides may be accomplished by any of a variety of standard means known in the art.

A preferred vector for screening peptides, but not necessarily preferred for the mass production of the peptides of the invention, is a recombinant DNA molecule containing a nucleotide sequence that codes for and is capable of expressing a fusion polypeptide containing, in the direction of amino- to carboxy-terminus, (1) a prokaryotic secretion signal domain, (2) a polypeptide of the invention, and, optionally, (3) a fusion protein domain. The vector includes DNA regulatory sequences for expressing the fusion polypeptide, preferably prokaryotic regulatory sequences. Such vectors can be constructed by those with skill in the art and have been described by Smith et at. (*Science* 228: 1315–1317, 1985), Clackson et al. (*Nature* 352:624–628, 1991); Kang et al. (in "Methods: A Companion to Methods in Enzymology: Vol. 2", R. A. Lerner and D. R. Burton, ed. Academic Press, NY, pp 111–118, 1991); Barbas et al. (*Proc. Natl. Acad. Sci. (USA)* 88:7978–7982, 1991), Roberts et al. (*Proc. Natl. Acad. Sci. (USA)* 89:2429–2433, 1992)

A fusion polypeptide may be useful for purification of the peptides of the invention. The fusion domain may, for example, include a poly-His tail which allows for purification on Ni+ columns or the maltose binding protein of the commercially available vector pMAL (New England BioLabs, Beverly, Mass.). A currently preferred, but by no means necessary, fusion domain is a filamentous phage membrane anchor. This domain is particularly useful for screening phage display libraries of monoclonal antibodies but may be of less utility for the mass production of antibodies. The filamentous phage membrane anchor is preferably a domain of the cpIII or cpVIII coat protein capable of associating with the matrix of a filamentous phage particle, thereby incorporating the fusion polypeptide onto the phage surface, to enable solid phase binding to specific antigens or epitopes and thereby allow enrichment and selection of the specific antibodies or fragments encoded by the phagemid vector.

The secretion signal is a leader peptide domain of a protein that targets the protein membrane of the host cell, such as the periplasmic membrane of gram negative bacteria. A preferred secretion signal for *E. coli* is a pelB secretion signal. The predicted amino acid residue sequences of the secretion signal domain from two pelB gene producing variants from *Erwinia carotova* are described in Lei, et al. (*Nature* 381:543–546, 1988). The leader sequence of the pelB protein has previously been used as a secretion signal for fusion proteins (Better, et al., *Science* 240:1041–1043, 1988; Sastry, et al., *Proc. Natl. Acad. Sci (USA)* 86:5728–5732, 1989; and Mullinax, et al., *Proc. Natl. Acad. Sci. (USA)* 87:8095–8099, 1990). Amino acid residue sequences for other secretion signal polypeptide domains from *E. coli* useful in this invention can be found in Oliver, In Neidhard, F. C. (ed.), *Escherichia coli* and *Salmonella Typhimurium*, American Society for Microbiology, Washington, D.C., 1:56–69 (1987).

To achieve high levels of gene expression in *E. coli*, it is necessary to use not only strong promoters to generate large quantities of mRNA, but also ribosome binding sites to ensure that the mRNA is efficiently translated. In *E. coli*, the ribosome binding site includes an initiation codon (AUG) and a sequence 3–9 nucleotides long located 3–11 nucleotides upstream from the initiation codon (Shine, et al., *Nature* 254:34, 1975). The sequence, AGGAGGU, which is called the Shine-Dalgarno (SD) sequence, is complementary to the 3' end of *E. coli* 16S rRNA. Binding of the ribosome to mRNA and the sequence at the 3' end of the mRNA can be affected by several factors: (i) the degree of complementarity between the SD sequence and 3' end of the 16S rRNA; (ii) the spacing and possibly the DNA sequence lying between the SD sequence and the AUG (Roberts, et al., *Proc. Natl. Acad. Sci.* (*USA*) 76:760.,1979a: Roberts, et al., *Proc. Natl. Acad. Sci.* (*USA*) 76:5596, 1979b; Guarente, et al., *Science* 209:1428, 1980; and Guarente, et al., *Cell* 20:543, 1980). Optimization is achieved by measuring the level of expression of genes in plasmids in which this spacing is systematically altered. Comparison of different mRNAs shows that there are statistically preferred sequences from positions −20 to +13 (where the A of the AUG is position 0) (Gold, et al., *Annu. Rev. Microbiol.* 35:365, 1981). Leader sequences have been shown to influence translation dramatically (Roberts, et al., 1979a, b supra); and (iii) the nucleotide sequence following the AUG, which affects ribosome binding (Taniguchi, et al., *J. Mol. Biol.*, 118:533, 1978).

The 3' regulatory sequences define at least one termination (stop) codon in frame with and operably joined to the heterologous fusion polypeptide.

In preferred embodiments with a prokaryotic expression host, the vector utilized includes a prokaryotic origin of replication or replicon, i.e., a DNA sequence having the ability to direct autonomous replication and maintenance of the recombinant DNA molecule extra-chromosomally in a prokaryotic host cell, such as a bacterial host cell, transformed therewith. Such origins of replication are well known in the art. Preferred origins of replication are those that are efficient in the host organism. A preferred host cell is *E. coli*. For use of a vector in *E. coli*, a preferred origin of replication is ColE1 found in pBR322 and a variety of other common plasmids. Also preferred is the p15A origin of replication found on pACYC and its derivatives. The ColE1 and p15A replicons have been extensively utilized in molecular biology, are available on a variety of plasmids and are described by Sambrook. et al., *Molecular Cloning: A Laboratory Manual,* 2nd edition, Cold Spring Harbor Laboratory Press, 1989).

In addition, those embodiments that include a prokaryotic replicon preferably also include a gene whose expression confers a selective advantage, such as drug resistance, to a bacterial host transformed therewith. Typical bacterial drug resistance genes are those that confer resistance to ampicillin, tetracycline, neomycin/kanamycin or chloramphenicol. Vectors typically also contain convenient restriction sites for insertion of translatable DNA sequences. Exemplary vectors are the plasmids pUC18 and pUC19 and derived vectors such as pcDNAII available from Invitrogen, (San Diego, Calif.).

When the peptide of the invention is an antibody including both heavy chain and light chain sequences, these sequences may be encoded on separate vectors or, more conveniently, may be expressed by a single vector. The heavy and light chain may, after translation or after secretion, form the heterodimeric structure of natural antibody molecules. Such a heterodimeric antibody may or may not be stabilized by disulfide bonds between the heavy and light chains.

A vector for expression of heterodimeric antibodies, such as the intact antibodies of the invention or the F(ab')$_2$, Fab or Fv fragment antibodies of the invention, is a recombinant DNA molecule adapted for receiving and expressing translatable first and second DNA sequences. That is, a DNA expression vector for expressing a heterodimeric antibody provides a system for independently cloning (inserting) the two translatable DNA sequences into two separate cassettes present in the vector, to form two separate cistrons for expressing the first and second polypeptides of a heterodimeric antibody. The DNA expression vector for expressing two cistrons is referred to as a dicistronic expression vector.

Preferably, the vector comprises a first cassette that includes upstream and downstream DNA regulatory sequences operably joined via a sequence of nucleotides adapted for directional ligation to an insert DNA. The upstream translatable sequence preferably encodes the secretion signal as described above. The cassette includes DNA regulatory sequences for expressing the first antibody polypeptide that is produced when an insert translatable DNA sequence (insert DNA) is directionally inserted into the cassette via the sequence of nucleotides adapted for directional ligation.

The dicistronic expression vector also contains a second cassette for expressing the second antibody polypeptide. The second cassette includes a second translatable DNA sequence that preferably encodes a secretion signal, as described above, operably joined at its 3' terminus via a sequence of nucleotides adapted for directional ligation to a downstream DNA sequence of the vector that typically defines at least one stop codon in the reading frame of the cassette. The second translatable DNA sequence is operably joined at its 5' terminus to DNA regulatory sequences forming the 5' elements. The second cassette is capable, upon insertion of a translatable DNA sequence (insert DNA), of expressing the second fusion polypeptide comprising a secretion signal with a polypeptide coded by the insert DNA.

The peptides of the present invention may also be produced by eukaryotic cells such as CHO cells, human hybridomas, immortalized B-lymphoblastoid cells, and the like. In this case, a vector is constructed in which eukaryotic regulatory sequences are operably joined to the nucleotide sequences encoding the peptide. The design and selection of an appropriate eukaryotic vector is within the ability and discretion of one of ordinary skill in the art. The subsequent purification of the peptides may be accomplished by any of a variety of standard means known in the art.

In another embodiment, the present invention provides host cells, both prokaryotic and eukaryotic, transformed or transfected with, and therefore including, the vectors of the present invention.

As used herein with respect to nucleic acids, the term "isolated" means: (i) amplified in vitro by, for example, polymerase chain reaction (PCR); (ii) recombinantly produced by cloning; (iii) purified, as by cleavage and gel separation; or (iv) synthesized by, for example, chemical synthesis. An isolated nucleic acid is one which is readily manipulable by recombinant DNA techniques well known in the art. Thus, a nucleotide sequence contained in a vector in which 5' and 3' restriction sites are known or for which polymerase chain reaction (PCR) primer sequences have been disclosed is considered isolated but a nucleic acid sequence existing in its native state in its natural host is not. An isolated nucleic acid may be substantially purified, but need not be. For example, a nucleic acid that is isolated within a cloning or expression vector is not pure in that it may comprise only a tiny percentage of the material in the cell in which it resides. Such a nucleic acid is isolated, however, as the term is used herein because it is readily manipulable by standard techniques known to those of ordinary skill in the art.

As used herein, a coding sequence and regulatory sequences are said to be "operably joined" when they are covalently linked in such a way as to place the expression or transcription of the coding sequence under the influence or control of the regulatory sequences. If it is desired that the coding sequences be translated into a functional protein, two DNA sequences are said to be operably joined if induction of a promoter in the 5' regulatory sequences results in the transcription of the coding sequence and if the nature of the linkage between the two DNA sequences does not (1) result in the introduction of a frame-shift mutation, (2) interfere with the ability of the promoter region to direct the transcription of the coding sequences, or (3) interfere with the ability of the corresponding RNA transcript to be translated into a protein. Thus, a promoter region would be operably joined to a coding sequence if the promoter region were capable of effecting transcription of that DNA sequence such that the resulting transcript might be translated into the desired protein or polypeptide.

The precise nature of the regulatory sequences needed for gene expression may vary between species or cell types, but shall in general include, as necessary, 5' non-transcribing and 5' non-translating sequences involved with initiation of transcription and translation respectively, such as a TATA box, capping sequence, CAAT sequence, and the like. Especially, such 5' non-transcribing regulatory sequences will include a promoter region which includes a promoter sequence for transcriptional control of the operably joined gene. Regulatory sequences may also include enhancer sequences or upstream activator sequences, as desired.

The invention also intends to embrace the use of the peptides described herein in in vivo and in vitro methods. In particular, the peptides can be used in detection methods as well as in treatment methods. The detection or diagnosis methods provided by the invention generally involve contacting one or more peptides of the invention with a sample in or from a subject. Preferably, the sample is first harvested from the subject, although in vivo detection methods are also envisioned. The sample may include any body tissue or fluid that is suspected of harboring the bacteria. A *P. aeruginosa* infection can affect any number of tissues including eye, ear, respiratory tract (including lung), heart (including heart valve), central nervous system, bone and joint, gastrointestinal tract (including large bowel), urinary tract, skin, and soft tissues. Lung or gastrointestinal lavages, or CNS fluid can all be sampled and tested for the presence of the bacteria.

In order to detect the bacteria, the sample is contacted with a peptide of the invention and the level of binding of the peptide is compared to the level of binding of the peptide to a sample that is known to be negative for the bacteria (i.e., a negative control). Peptides that are conjugated to a detectable label are most useful in these assays. Methods of conjugating peptides to detectable labels or cytotoxic agents are described in greater detail above.

The invention also embraces methods of detecting *P. aeruginosa* in or on medical equipment, surfaces, instrumentation, and the like, in order to identify contamination of the bacteria. These detection methods are carried out essentially in the same manner as those described above. The items and surfaces to be tested are either contacted directly with the peptides of the invention, or alternatively, they are sampled and the sample is tested for the presence of the bacteria. Sampling can include but is not limited to swabbing, wiping, flushing, and the like.

As used herein, the term "treatment" refers to the administration of peptides to a subject for the purpose of achieving a medically desirable benefit. Accordingly, "treatment" intends to embrace both "prophylactic" and "therapeutic" treatment methods. Prophylactic treatment methods refer to treatment administered to a subject prior to the diagnosis of a *P. aeruginosa* infection or a *P. aeruginosa* related condition. In other words, the subject does not present with symptoms of either a *P. aeruginosa* infection or a *P. aeruginosa* related condition although the subject may be at risk of either. Therapeutic treatment methods refer to treatment administered to a subject after the diagnosis of a *P. aeruginosa* infection or a *P. aeruginosa* related condition. In other words, the subject has been diagnosed as having either a *P. aeruginosa* infection or a *P. aeruginosa* related condition or alternatively, the subject may exhibit symptoms associated with either.

As used herein, a subject is a human, non-human primate, cow, horse, pig, sheep, goat, dog, cat or rodent. In all embodiments, human subjects are preferred.

When used therapeutically, an effective amount is that amount which inhibits the *P. aeruginosa* infection. Such inhibition may be measured by a partial or complete inhibition of bacterial cell proliferation or, in some instances, partial or complete elimination of bacterial colonies, which can generally be measured by a reduction in number of bacteria or bacterial colonies. When used prophylactically, an effective amount is that amount which prevents a *P. aeruginosa* infection from arising. Such inhibition may be measured by an absence of bacteria in a lung lavage from, for example, subjects having cystic fibrosis or subjects at risk of developing cystic fibrosis. Generally, a therapeutically effective amount may vary with the subject's age, condition, and sex, as well as the extent of the disease in the subject and can be determined by one of skill in the art. The dosage may be adjusted by the individual physician in the event of any complication.

The present invention also includes a method for treating a *P. aeruginosa* related disorder. A "*P. aeruginosa* related disorder" as used herein is any disorder associated with the presence of *P. aeruginosa* infection. These disorders include cystic fibrosis, ulcerative keratitis, pneumonia, bacteremia, organ and tissue infection such as kidney, bladder, liver, brain, skin, muscle, lymph node or sinus infection. The method involves the step of administering a peptide of the invention to a subject having such a disorder in an amount effective to inhibit the disorder. The disorder is "inhibited" if symptoms associated with the disorder are lessened. In some instances, this amount may be similar to that required to inhibit a *P. aeruginosa* infection in the subject.

An effective amount typically will vary from about 0.01 mg/kg to about 1000 mg/kg, S more typically from about 0.1 mg/kg to about 200 mg/kg, and often from about 0.2 mg/kg to about 20 mg/kg, in one or more dose administrations daily, for one or several days (depending of course of the mode of administration and the factors discussed above).

One of skill in the art can determine what an effective amount of a peptide is by screening the ability of the peptide to bind to *P. aeruginosa* MEP and optionally to enhance opsonization and phagocytosis in vitro. Exemplary assays for measuring the ability of a peptide of the invention to bind to *P. aeruginosa* MEP and optionally to enhance opsonization and phagocytosis are provided in the Examples and have been discussed above.

According to the methods of the invention, the peptide may be administered in a pharmaceutical composition. In general, a pharmaceutical composition comprises the peptide of the invention and a pharmaceutically-acceptable carrier. Pharmaceutically-acceptable carriers for peptides, monoclonal antibodies, and antibody fragments are well-known to those of ordinary skill in the art. As used herein, a pharmaceutically-acceptable carrier means a non-toxic material that does not interfere with the effectiveness of the biological activity of the active ingredients, i.e., the ability of the peptide to bind to *P. aeruginosa* MEP and optionally to enhance opsonization and phagocytosis.

Pharmaceutically acceptable carriers include diluents, fillers, salts, buffers, stabilizers, solubilizers and other materials which are well-known in the art. Exemplary pharmaceutically acceptable carriers for peptides in particular are described in U.S. Pat. No. 5,211,657. Such preparations may routinely contain salt, buffering agents, preservatives, compatible carriers, and optionally other therapeutic agents. When used in medicine, the salts should be pharmaceutically acceptable, but non-pharmaceutically acceptable salts may conveniently be used to prepare pharmaceutically-acceptable salts thereof and are not excluded from the scope of the invention. Such pharmacologically and pharmaceutically-acceptable salts include, but are not limited to, those prepared from the following acids: hydrochloric, hydrobromic, sulfuric, nitric, phosphoric, maleic, acetic, salicylic, citric, formic, malonic, succinic, and the like. Also, pharmaceutically-acceptable salts can be prepared as alkaline metal or alkaline earth salts, such as sodium, potassium or calcium salts.

The peptides of the invention may be formulated into preparations in solid, semi-solid, liquid or gaseous forms such as tablets, capsules, powders, granules, ointments, solutions, depositories, inhalants and injections, and usual ways for oral, parenteral or surgical administration. The invention also embraces pharmaceutical compositions which are formulated for local administration, such as by implants.

A variety of administration routes are available. The methods of the invention, generally speaking, may be practiced using any mode of administration that is medically acceptable, meaning any mode that produces effective levels of the active compounds without causing clinically unacceptable adverse effects. According to the methods of the invention the peptides can be administered by injection, by gradual infusion over time or by any other medically acceptable mode. Such modes of administration include oral, rectal, topical, nasal, interdermal, or parenteral routes. The term "parenteral" includes subcutaneous, intravenous, intramuscular, or infusion. Intravenous or intramuscular routes are not particularly suitable for long-term therapy and prophylaxis. They could, however, be preferred in emergency situations. Oral administration may be preferred for prophylactic treatment because of the convenience to the patient as well as the dosing schedule. Compositions suitable for oral administration may be presented as discrete units, such as capsules, tablets, lozenges, each containing a predetermined amount of the active agent. Other compositions include suspensions in aqueous liquids or non-aqueous liquids such as a syrup, elixir or an emulsion.

When the compounds described herein (including peptide and non-peptide varieties) are used therapeutically, in certain embodiments a desirable route of administration may be by pulmonary aerosol. Techniques for preparing aerosol delivery systems containing compounds are well known to those of skill in the art. Generally, such systems should utilize components which will not significantly impair the biological properties of the peptides (see, for example, Sciarra and Cutie, "Aerosols," in *Remington's Pharmaceutical Sciences,* 18th edition, 1990, pp 1694–1712; incorporated by reference). Those of skill in the art can readily determine the various parameters and conditions for producing aerosols without resort to undue experimentation.

The methods of the invention also encompass the step of administering the peptides of the invention in conjunction with conventional therapies for treating the underlying bacterial infection. For example, the method of the invention may be practiced simultaneously with a conventional treatment, such as for example antibiotic therapy. In some embodiments, the peptides may be administered substantially simultaneously with the conventional treatment. By substantially simultaneously, it is meant that a peptide of the invention is administered to a subject close enough in time with the administration of the conventional treatment (e.g., antibiotic), whereby the two compounds may exert an additive or even synergistic effect. In some instances, the peptide and the agent of the conventional treatment are conjugated to each other. In others, the compounds are physically separate.

The peptides of the invention may be administered directly to a tissue. Preferably, the tissue is one in which the bacterial infection exists, such as for example, the lungs in cystic fibrosis patients. Alternatively, the tissue is one in which the infection is likely to arise. Direct tissue administration may be achieved by direct injection. The peptides may be administered once, or alternatively they may be administered in a plurality of administrations. If administered multiple times, the peptides may be administered via different routes. For example, the first (or the first few) administrations may be made directly into the affected tissue while later administrations may be systemic.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like. Lower doses will result from other forms of administration, such as intravenous administration. In the event that a response in a subject is insufficient at the initial doses applied, higher doses (or effectively higher doses by a different, more localized delivery route) may be employed to the extent that patient tolerance permits. Multiple doses per day are contemplated to achieve appropriate systemic levels of compounds.

In yet other embodiments, the preferred vehicle is a biocompatible microparticle or implant that is suitable for implantation into the mammalian recipient. Exemplary bioerodible implants that are useful in accordance with this method are described in PCT International Application No. PCT/US/03307 (Publication No. WO 95/24929, entitled "Polymeric Gene Delivery System", claiming priority to U.S. patent application Ser. No. 213,668, filed Mar. 15, 1994). PCT/US/0307 describes a biocompatible, preferably biodegradable polymeric matrix for containing a biological macromolecule. The polymeric matrix may be used to achieve sustained release of the agent in a subject. In accordance with one aspect of the instant invention, the agent described herein may be encapsulated or dispersed within the biocompatible, preferably biodegradable polymeric matrix disclosed in PCT/US/03307. The polymeric matrix preferably is in the form of a microparticle such as a microsphere (wherein the agent is dispersed throughout a solid polymeric matrix) or a microcapsule (wherein the agent is stored in the core of a polymeric shell). Other forms of the polymeric matrix for containing the agent include films, coatings, gels, implants, and stents. The size and composition of the polymeric matrix device is selected to result in favorable release kinetics in the tissue into which the matrix device is implanted. The size of the polymeric matrix device further is selected according to the method of delivery which is to be used, typically injection into a tissue or administration of a suspension by aerosol into the nasal and/or pulmonary areas. The polymeric matrix composition can be selected to have both favorable degradation rates and also to be formed of a material which is bioadhesive, to further increase the effectiveness of transfer when the device is administered to a vascular, pulmonary, or other surface. The matrix composition also can be selected not to degrade, but rather, to release by diffusion over an extended period of time.

Both non-biodegradable and biodegradable polymeric matrices can be used to deliver the agents of the invention to the subject. Biodegradable matrices are preferred. Such polymers may be natural or synthetic polymers. Synthetic polymers are preferred. The polymer is selected based on the period of time over which release is desired, generally in the order of a few hours to a year or longer. Typically, release over a period ranging from between a few hours and three to twelve months is most desirable. The polymer optionally is in the form of a hydrogel that can absorb up to about 90% of its weight in water and further, optionally is cross-linked with multivalent ions or other polymers.

In general, the agents of the invention may be delivered using the bioerodible implant by way of diffusion, or more preferably, by degradation of the polymeric matrix. Exemplary synthetic polymers which can be used to form the biodegradable delivery system include: polyamides, polycarbonates, polyalkylenes, polyalkylene glycols, polyalkylene oxides, polyalkylene terepthalates, polyvinyl alcohols, polyvinyl ethers, polyvinyl esters, poly-vinyl halides, polyvinylpyrrolidone, polyglycolides, polysiloxanes, polyurethanes and co-polymers thereof, alkyl cellulose, hydroxyalkyl celluloses, cellulose ethers, cellulose esters, nitro celluloses, polymers of acrylic and methacrylic esters, methyl cellulose, ethyl cellulose, hydroxypropyl cellulose, hydroxy-propyl methyl cellulose, hydroxybutyl methyl cellulose, cellulose acetate, cellulose propionate, cellulose acetate butyrate, cellulose acetate phthalate, carboxylethyl cellulose, cellulose triacetate, cellulose sulphate sodium salt, poly(methyl methacrylate), poly(ethyl methacrylate), poly(butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), poly(octadecyl acrylate), polyethylene, polypropylene, poly(ethylene glycol), poly(ethylene oxide), poly(ethylene terephthalate), poly(vinyl alcohols), polyvinyl acetate, poly vinyl chloride, polystyrene and polyvinylpyrrolidone.

Examples of non-biodegradable polymers include ethylene vinyl acetate, poly(meth)acrylic acid, polyamides, copolymers and mixtures thereof.

Examples of biodegradable polymers include synthetic polymers such as polymers of lactic acid and glycolic acid, polyanhydrides, poly(ortho)esters, polyurethanes, poly(butic acid), poly(valeric acid), and poly(lactide-cocaprolactone), and natural polymers such as alginate and other polysaccharides including dextran and cellulose, collagen, chemical derivatives thereof (substitutions, additions of chemical groups, for example, alkyl, alkylene, hydroxylations, oxidations, and other modifications routinely made by those skilled in the art), albumin and other hydrophilic proteins, zein and other prolamines and hydrophobic proteins, copolymers and mixtures thereof. In general, these materials degrade either by enzymatic hydrolysis or exposure to water in vivo, by surface or bulk erosion.

Bioadhesive polymers of particular interest include bioerodible hydrogels described by H. S. Sawhney, C. P. Pathak and J. A. Hubell in Macromolecules, 1993, 26, 581–587, the teachings of which are incorporated herein, polyhyaluronic acids, casein, gelatin, glutin, polyanhydrides, polyacrylic acid, alginate, chitosan, poly(methyl methacrylates), poly(ethyl methacrylates), poly(butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), and poly(octadecyl acrylate).

Other delivery systems can include time-release, delayed release or sustained release delivery systems. Such systems can avoid repeated administrations of the peptide, increasing convenience to the subject and the physician. Many types of release delivery systems are available and known to those of ordinary skill in the art. They include polymer base systems such as poly(lactide-glycolide), copolyoxalates, polycaprolactones, polyesteramides, polyorthoesters, polyhydroxybutyric acid, and polyanhydrides. Microcapsules of the foregoing polymers containing drugs are described in, for example, U.S. Pat. No. 5,075,109. Delivery systems also include non-polymer systems that are: lipids including sterols such as cholesterol, cholesterol esters and fatty acids or neutral fats such as mono- di- and triglycerides; hydrogel release systems; silastic systems; peptide based systems; wax coatings; compressed tablets using conventional binders and excipients; partially fused implants; and the like. Specific examples include, but are not limited to: (a) erosional systems in which the platelet reducing agent is contained in a form within a matrix such as those described in U.S. Pat. Nos. 4,452,775, 4,675,189, and 5,736,152 and (b) diffusional systems in which an active component permeates at a controlled rate from a polymer such as described in U.S. Pat. Nos. 3,854,480, 5,133,974 and 5,407,686. In addition, pump-based hardware delivery systems can be used, some of which are adapted for implantation.

Use of a long-term sustained release implant may be particularly suitable for prophylactic treatment of subjects at risk of developing a *P. aeruginosa* infection. Long-term release, as used herein, means that the implant is constructed and arranged to delivery therapeutic levels of the active ingredient for at least 30 days, and preferably 60 days. Long-term sustained release implants are well-known to those of ordinary skill in the art and include some of the release systems described above.

The following examples are provided to illustrate specific instances of the practice of the present invention and are not intended to limit the scope of the invention. As will be apparent to one of ordinary skill in the art, the present invention will find application in a variety of compositions and methods.

EXAMPLES

Example 1

Materials and Methods:

Immunization of Patients with MEP: Culture of *P. aeruginosa*, purification of MEP, and immunization of subjects with MEP has been described before in U.S. Pat. No. 4,578,458, the entire contents of which are incorporated herein by reference. Briefly, subjects are preferably immunized with purified MEP harvested from *P. aeruginosa* 2192 isolates (ATCC No. 39324). Although *P. aeruginosa* strain 2192 is preferred, new strains that produce a polysaccharide having essentially the same antigenic determinants as present in *P. aeruginosa* 2192 may also be used. *P. aeruginosa* can be maintained in liquid basal medium containing essential nutrients and ingredients (e.g., Mian's Minimal Medium, Trypticase Soy Broth and deoxycholate citrate agar, preferably supplemented with divalent cations such as magnesium). Methods of bacterial culture are known in the art. MEP is purified from Mian's minimal medium, followed by precipitation of MEP with alcohol. The precipitate is then digested with DNase and RNase, followed by separation on a Sephacel S-300 column, precipitation and lyophilization. The material is treated with 1% acetic acid at 95° C. for 1–3 hours, cooled, and then the precipitate is removed by centrifugation and the supernate is dialyzed and lyophilized. This procedure results in greater than 99% purity. For administration to a subject, the lyophilized precipitate is reconstituted in a pharmaceutically acceptable carrier. The amount of MEP administered corresponds to that amount required to elicit antibody formation at a concentration at least 4 times greater than that which existed prior to administration. Generally, this amount is 10–500 µg/dose.

Harvest of B Cells Transformation with EBV and Screening Assays: Human blood is collected from subjects seven days after having been administered MEP. Peripheral blood mononuclear cells are isolated from the blood by ficoll-hypaque sedimentation and transformed with EBV as described by Posner et al. (Autoimmunity, 8:149–158, 1990). Transformed B cells are screened for their ability to recognize and bind to *P. aeruginosa* colonies in vitro using ELISA. Transformed B cells secreting antibody are fused with the immortalized cell line fusion partner HMMA 2.5 as described by Posner et al. (Hybridoma, 6:611–625, 1987).

Clones are screened for the ability to recognize and bind to *P. aeruginosa* colonies in vitro using ELISA. ELISA plates are coated with 10 µg MEP per ml of 0.04 M phosphate buffer, pH 7.4 for 2 hours at 37° C. After washing, 1% skim milk is added for 1 hour at 37° C. following which plates are washed again. Supernatants are incubated on the plates for 1 hour at 37° C. After washing with PBS, horseradish peroxidase conjugated antibody goat anti-human IgG and goat anti-human IgA are added for 1 hour at 37° C. Positive wells are selected by color change upon adding the substrate o-phenylediamine.

Cloning of Variable Regions; Isotype Switching: MEP specific immortalized fusion B cell clones are then further analyzed in order to derive the sequences of MEP specific antibodies. RNA is isolated from each clone separately, and cDNA is subsequently prepared. Human Ig light chain variable region DNA was amplified from the cDNA by the polymerase chain reaction (PCR) using a set of DNA primers with homology to human light chain signal sequences at the 5' end and human light chain C region at the 3' end. This amplified DNA fragment was inserted directly into an expression plasmid (TCAE 5.3) in front of the human κ light chain constant domain and the entire construct was sequenced. Similarly, a human Ig heavy chain variable region DNA was amplified from the cDNA using PCR and a set of primers with homology to the human heavy chain signal sequence at the 5' end and human heavy chain $CH_1$ region at the 3' end. This latter amplified DNA fragment was inserted into the TCAE 5.3 expression plasmid in front of the human IgG1 heavy chain constant domain and the entire construct was sequenced. TCAE 5.3 is a human Ig expression vector that has been described by Reff et al. Blood 83:435–445, 1994. It contains human IgG1 heavy chain and human kappa light chain constant region genes on the same plasmid.

The resultant expression vectors were introduced into a Chinese Hamster Ovary (CHO) cell line DGH44 (obtained from Dr. Larry Chasin, Columbia University, New York) either by DNA-liposome-mediated transfection or by electroporation, as described by Preston et al. Infection and Immunity 66:4137–4142, 1998, and by Reff et al. Blood 83:435–445, 1994. The supernatant in which the transfected CHO cell line was grown was tested for antibody production using ELISA. Antibodies were purified from culture supernatant using protein G affinity chromatography (for IgG isotypes) and lectin Jacalin affinity chromatography (for IgA isotype).

Results:

Three clones of transformed human B cells from an individual immunized with a MEP vaccine were obtained. These clones were identified on the basis of their ability to produce an antibody that bound to the purified MEP antigen. All three were of the IgA/lambda isotype. They were designated F428, F429 and F431.

The nucleotide sequence encoding the variable regions of the light and heavy chains of each of these three clones was determined. From the three clones, two different heavy chain sequences and two different light chain sequences were identified, in the following combinations:

| Clone | Heavy Chain | Light Chain |
| --- | --- | --- |
| F428 | A | 1 |
| F429 | A | 2 |
| F431 | B | 1 |
| COMB | B | 2 |

A fourth antibody molecule was constructed using the B heavy chain and second light chain to produce an antibody labeled "COMB" (for combination). Thus recombinant antibody molecules containing all four possible pairs of heavy and light chains identified among the original three clones have been constructed and expressed.

The following data contain nucleotide and amino acid sequence information for the two different heavy chains and two different light chains.

Nucleotide sequence of the variable region of the heavy chain of human monoclonal antibodies F428 and F429 specific to the P. aeruginosa MEP antigen starting with the first nucleotide for the initial amino acid in the first framework region (FAR) and ending with the last nucleotide for the end of the variable region (i.e., SEQ ID NO:1):

CAGCTGCAGCTGCAGGAGTCGGGCCCCGGACTGGTGAAGCCTACGGAGAC

CCTGTCCCTCACCTGCACTGTCTCTGGTGGCCCCATCACCTATATTAATT

ACTACTGGGGCTGGGTCCGCCAGCCCCAGGGAAGGGGCTGGAGTGGATT

GGGAGTATCCATTATGATGGGAGCACCTTCTACAACCCGTCCCTCAAGAG

TCGCGTCACCATATCAGGAGACACGTCCAAGAGCGAGTTCTCTGTGAAGC

TGAGTTCTGTGACCGCCGCGGACACGGCCGTCTATTACTGTGCGAGAACG

TATTACGATGCTTCGGGGAGCCCTTACTTTGACCACTGGGGCCAGGGAAC

CCTGGTCACCGTCTCCTCA

Nucleotide sequence of the framework region 1 (FR1) of the heavy chain of human monoclonal antibodies F428 and F429 (i.e., SEQ ID NO:33):

CAGCTGCAGCTGCAGGAGTCGGGCCCCGGACTGGTGAAGCCTACGGAGAC

CCTGTCCCTCACCTGCACTGTCTCTGGTGGCCCCATCACC.

Nucleotide sequence of CDR1 of the heavy chain of human monoclonal antibodies F428 and F429 (i.e., SEQ ID NO:9): TATATTAATTACTACTGGGGC.

Nucleotide sequence of the FR2 of the heavy chain of human monoclonal antibodies F428 and F429 (i.e., SEQ ID NO:34): TGGGTCCGCCAGCCCCAGG-GAAGGGGCTGGAGTGGATTGGG.

Nucleotide sequence of CDR2 of the heavy chain of human monoclonal antibodies F428 and F429 (i.e., SEQ ID NO:10): AGTATCCATTATGATGGGAGCACCTTC-TACAACCCGTCCCTCAAGAGT.

Nucleotide sequence of the FR3 of the heavy chain of human monoclonal antibodies F428 and F429 (i.e., SEQ ID NO:35):

CGCGTCACCATATCAGGAGACACGTCCAAGAGCGAGTTCTCTGTGAAGCT

GAGTTCTGTGACCGCCGCGGACACGGCCGTCTATTACTGTGCGAGA.

Nucleotide sequence of CDR3 of the heavy chain of human monoclonal antibodies F428 and F429 (i.e., SEQ ID NO:11): ACGTATTACGATGCTTCGGGGAGCCCT-TACTTTGACCAC.

Nucleotide sequence of the FR4 of the heavy chain of human monoclonal antibodies F428 and F429 (i.e., SEQ ID NO:36): TGGGGCCAGGGAACCCTGGTCAC-CGTCTCCTCA.

Single amino acid sequence of the variable region of the heavy chain of human monoclonal antibodies F428 and F429 specific to the P. aeruginosa MEP antigen (i.e., SEQ ID NO:5):

QLQLQESGPGLVKPTETLSLTCTVSGGPITYINYYWGWVRQPPGKGLEWI

GSLHYDGSTFYNPSLKSRVTISGDTSKSEFSVKLSSVTAADTAVYYCART

YYDASGSPYFDHWGQGTLVTVSS

Single amino acid sequence of FR1 of the heavy chain of human monoclonal antibodies F428 and F429 specific to the P. aeruginosa MEP antigen (i.e., SEQ ID NO:49): QLQLQESGPGLVKPTETLSLTCTVSGGPIT.

Single amino acid sequence of CDR1 of the heavy chain of human monoclonal antibodies F428 and F429 specific to the P. aeruginosa MEP antigen (i.e., SEQ ID NO:21): YINYYWG.

Single amino acid sequence of FR2 of the heavy chain of human monoclonal antibodies F428 and F429 specific to the P. aeruginosa MEP antigen (i.e., SEQ ID NO:50): WVRQP-PGKGLEWIG.

Single amino acid sequence of CDR2 of the heavy chain of human monoclonal antibodies F428 and F429 specific to the P. aeruginosa MEP antigen (i.e., SEQ ID NO:22): SIHYDGSTFYNPSLKS.

Single amino acid sequence of FR3 of the heavy chain of human monoclonal antibodies F428 and F429 specific to the P. aeruginosa MEP antigen (i.e., SEQ ID NO:51): RVTIS-GDTSKSEFSVKLSSVTAADTAVYYCAR.

Single amino acid sequence of CDR2 of the heavy chain of human monoclonal antibodies F428 and F429 specific to the P. aeruginosa MEP antigen (i.e., SEQ ID NO:23): TYYDASGSPYFDH.

Single amino acid sequence of FR4 of the heavy chain of human monoclonal antibodies F428 and F429 specific to the P. aeruginosa MEP antigen (i.e., SEQ ID NO:52): WGQGTLVTVSS.

Nucleotide sequence of the variable region of the light chain of human monoclonal antibodies F428 and F431 specific to the P. aeruginosa MEP antigen (SEQ ID NO: 2):

CAGTCTGTGTTGACGCAGCCGCCCTCAGTGTCTGCGGCCCCAGGACAGAG

GGTCACCATCTCCTGCTCTGGAAGCAGCTCCAACCTTGGGAACAATTTTG

TATCCTGGTACCAGCAACTCCCAGGAGCAGCCCCCCGGCTCCTCATTTAT

GACAATGATAAGCGACCCTCAGGGATTCCTGACCGATTCTCTGGCTCCAA

GTCTGGCACGTCAGCCACCCTGGGCATCACCGGGCTCCAGACTGGGGACG

AGGCCGATTATTACTGCGGAACATGGGATAGCAGCCTGACTGCTTATGTC

TTCGGAAGTGGGACCAAGGTCACCGTCCTA.

Nucleotide sequence of FR1 of the heavy chain of human monoclonal antibodies F428 and F431 (i.e., SEQ ID NO:37):

CAGTCTGTGTTGACGCAGCCGCCCTCAGTGTCTGCGGCCCCAGGACAGAG

GGTCACCATCTCCTGC.

Nucleotide sequence of CDR1 of the heavy chain of human monoclonal antibodies F428 and F431 (i.e., SEQ ID NO:12): TCTGGAAGCAGCTCCAACCTTGGGAA-CAATTTTGTATCC.

Nucleotide sequence of the FR2 of the heavy chain of human monoclonal antibodies F428 and F431 (i.e., SEQ ID NO:38): TGGTACCAGCAACTCCCAGGAGCAGCCCCCCGGCTCCTCATTTAT.

Nucleotide sequence of CDR2 of the heavy chain of human monoclonal antibodies F428 and F431 (i.e., SEQ ID NO:13): GACAATGATAAGCGACCCTCA.

Nucleotide sequence of the FR3 of the heavy chain of human monoclonal antibodies F428 and F431 (i.e., SEQ ID NO:39):

GGGATTCCTGACCGATTCTCTGGCTCCAAGTCTGGCACGTCAGCCACCCT

GGGCATCACCGGGCTCCAG ACTGGGGACGAGGCCGATTATTACTGC.

Nucleotide sequence of CDR3 of the heavy chain of human monoclonal antibodies F429 and F431 (i.e., SEQ ID NO:14): GGAACATGGGATAGCAGCCTGACTGCTTATGTC.

Nucleotide sequence of the FR4 of the heavy chain of human monoclonal antibodies F428 and F431 (i.e., SEQ ID NO:40): TTCGGAAGTGGGACCAAGGTCACCGTCCTA.

Single amino acid sequence of the variable region of the heavy chain of human monoclonal antibodies F428 and F431 specific to the *P. aeruginosa* MEP antigen (i.e., SEQ ID NO:6):

QSVLTQPPSVSAAPGQRVTISCSGSSSNLGNNFVSWYQQLPGAAPRLLIY

DNDKRPSGIPDRFSGSKSGTSATLGITGLQTGDEADYYCGTWDSSLTAYV

FGSGTKVTV

Single amino acid sequence of FR1 of the heavy chain of human monoclonal antibodies F428 and F431 specific to the *P. aeruginosa* MEP antigen (i.e., SEQ ID NO:53): QSVLTQPPSVSAAPGQRVTISC.

Single amino acid sequence of CDR1 of the heavy chain of human monoclonal antibodies F428 and F431 specific to the *P. aeruginosa* MEP antigen (i.e., SEQ ID NO:24): SGSSSNLGNNFVS.

Single amino acid sequence of FR2 of the heavy chain of human monoclonal antibodies F428 and F431 specific to the *P. aeruginosa* MEP antigen (i.e., SEQ ID NO:54): WYQQLPGAAPRLLIY.

Single amino acid sequence of CDR2 of the heavy chain of human monoclonal antibodies F428 and F431 specific to the *P. aeruginosa* MEP antigen (i.e., SEQ ID NO:25): DNDKRPS.

Single amino acid sequence of FR3 of the heavy chain of human monoclonal antibodies F428 and F431 specific to the *P. aeruginosa* MEP antigen (i.e., SEQ ID NO:55): GIPDRFSGSKSGTSATLGITGLQTGDEADYYC.

Single amino acid sequence of CDR3 of the heavy chain of human monoclonal antibodies F428 and F431 specific to the *P. aeruginosa* MEP antigen (i.e., SEQ ID NO:26): GTWDSSLTAYV.

Single amino acid sequence of FR4 of the light chain of human monoclonal antibodies F428 and F431 specific to the *P. aeruginosa* MEP antigen (i.e., SEQ ID NO:56): FGSGTKVTV.

Nucleotide sequence of the variable region of the light chain of human monoclonal antibodies F429 and COMB specific to the *P. aeruginosa* MEP antigen (SEQ ID NO: 3):

CAGTCTGTGTTGACGCAGCCGCCCTCAGTGTCTGCGGCCCCAGGACAGAA

GGTCTCCATCTCCTGCTCTGGAAGCAGCTCCAACATTGGGAATAATTATG

TATCCTGGTACCAGCAGCTCCCAGGAACAGCCCCCAATCTCCTCATTTAT

GACAATAATAAGCGACCCTCAGGGATTCCGGACCGATTCTCTGGCTCCAA

GTCTGGCACGTCAGCCACCCTGGACATCACCGGACTCCAGAGTGGGGACG

AGGCCGATTATTACTGCGGAACATGGGATAGCAGCCTGAGTACTTGGGTG

TTCGGCGGAGGGACCAAACTGACCGTCCTA.

Nucleotide sequence of FR1 of the light chain of human monoclonal antibodies F429 and COMB (i.e., SEQ ID NO:41):

CAGTCTGTGTTGACGCAGCCGCCCTCAGTGTCTGCGGCCCCAGGACAGAA

GGTCTCCATCTCCTGC.

Nucleotide sequence of CDR1 of the light chain of human monoclonal antibodies F429 and COMB (i.e., SEQ ID NO:15): TCTGGAAGCAGCTCCAACATTGGGAATAATTATGTATCC.

Nucleotide sequence of the FR2 of the light chain of human monoclonal antibodies F429 and COMB (i.e., SEQ ID NO:42): TGGTACCAGCAGCTCCCAGGAACAGCCCCCAATCTCCTCATTTAT.

Nucleotide sequence of CDR2 of the light chain of human monoclonal antibodies F429 and COMB (i.e., SEQ ID NO:16): GACAATAATAAGCGACCCTCA.

Nucleotide sequence of the FR3 of the light chain of human monoclonal antibodies F429 and COMB (i.e., SEQ ID NO:43):

GGGATTCCGGACCGATTCTCTGGCTCCAAGTCTGGCACGTCAGCCACCCT

GGACATCACCGGACTCCAGAGTGGGGACGAGGCCGATTATTACTGC.

Nucleotide sequence of CDR3 of the light chain of human monoclonal antibodies F429 and COMB (i.e., SEQ ID NO:17): GGAACATGGGATAGCAGCCTGAGTACTGGGTG.

Nucleotide sequence of the FR4 of the light chain of human monoclonal antibodies F429 and COMB (i.e., SEQ ID NO:44): TTCGGCGGAGGGACCAAACTGACCGTCCTA.

Single amino acid sequence of the variable region of the light chain of human monoclonal antibodies F429 and COMB specific to the *P. aeruginosa* MEP antigen (i.e., SEQ ID NO:7):

QSVLTQPPSVSAAPGQKVSISCSGSSSNIGNNYVSWYQQLPGTAPNLLIY

DNNKRPSGIPDRFSGSKSGTSATLDITGLQSGDEADYYCGTWDSSLSTWV

FGGGTKLTVL.

Single amino acid sequence of FR1 of the light chain of human monoclonal antibodies F429 and COMB specific to the *P. aeruginosa* MEP antigen (i.e., SEQ ID NO:57): QSVLTQPPSVSAAPGQKVSISC.

Single amino acid sequence of CDR1 of the light chain of human monoclonal antibodies F429 and COMB specific to the *P. aeruginosa* MEP antigen (i.e., SEQ ID NO:27): SGSSSNIGNNYVS.

Single amino acid sequence of FR2 of the light chain of human monoclonal antibodies F429 and COMB specific to the *P. aeruginosa* MEP antigen (i.e., SEQ ID NO:58): WYQQLPGTAPNLLIY.

Single amino acid sequence of CDR2 of the light chain of human monoclonal antibodies F429 and COMB specific to the *P. aeruginosa* MEP antigen (i.e., SEQ ID NO:28): DNNKRPS.

Single amino acid sequence of FR3 of the light chain of human monoclonal antibodies F429 and COMB specific to the *P. aeruginosa* MEP antigen (i.e., SEQ ID NO:59): GIPDRFSGSKSGTSATLDITGLQSGDEADYYC.

Single amino acid sequence of CDR3 of the light chain of human monoclonal antibodies F429 and COMB specific to the *P. aeruginosa* MEP antigen (i.e., SEQ ID NO:29): GTWDSSLSTWV.

Single amino acid sequence of FR4 of the light chain of human monoclonal antibodies F429 and COMB specific to the *P. aeruginosa* MEP antigen (i.e., SEQ ID NO:60): FGGGTKLTVL.

Nucleotide sequence of the variable region of the heavy chain of human monoclonal antibodies F431 and COMB specific to the *P. aeruginosa* MEP antigen (SEQ ID NO:4):

CAGCTGCACCTGCAGGAGTCGGGCCCAGGACTAGTGAAGCCTTCGGAGAC

CCTGTCCCTCACGTGCACTGTCTCTGGTGGCCCCATCACCAGTAATAATT

ACTACTGGGGCTGGATCCGCCAGCCCCAGGGAAGGGGCTGGAGTGGATT

GGGACTATCTCTTATAATGGGTACACCTACTACATCCCGTCCCTCAGGGG

TCGAGTCACCATATCCGGAGACACGTCCAAGAACCAGTTCTCCCTGAGGG

TGAACTCTGTGACCGCCGCAGACACGGCTATGTATTACTGTGCGAGACAT

GACTATAGCATGTCGTCCGGACTTACTGACAACTGGTTCGACCCCTGGGG

CCAGGGAACCCTGGTCACCGTCTCCTCA.

Nucleotide sequence of FR1 of the heavy chain of human monoclonal antibodies F431 and COMB (i.e., SEQ ID NO:45):

CAGCTGCACCTGCAGGAGTCGGGCCCAGGACTAGTGAAGCCTTCGGAGAC

CCTGTCCCTCACGTGCACTGTCTCTGGTGGCCCCATCACC.

Nucleotide sequence of CDR1 of the heavy chain of human monoclonal antibodies F431 and COMB (i.e., SEQ ID NO:18): AGTAATAATTACTACTGGGGC.

Nucleotide sequence of the FR2 of the heavy chain of human monoclonal antibodies F431 and COMB (i.e., SEQ ID NO:46): TGGATCCGCCAGCCCCAGG-GAAGGGGCTGGAGTGGATTGGG.

Nucleotide sequence of CDR2 of the heavy chain of human monoclonal antibodies F431 and COMB (i.e., SEQ ID NO:19): ACTATCTCTTATAATGGGTACACCTAC-TACATCCCGTCCCTCAGGGGT.

Nucleotide sequence of the FR3 of the heavy chain of human monoclonal antibodies F431 and COMB (i.e., SEQ ID NO:47):

CGAGTCACCATATCCGGAGACACGTCCAAGAACCAGTTCTCCCTGAGGGT

GAACTCTGTGACCGCCGCAGACACGGCTATGTATTACTGTGCGAG.

Nucleotide sequence of CDR3 of the heavy chain of human monoclonal antibodies F431 and COMB (i.e., SEQ ID NO:20): CATGACTATAGCATGTCGTCCGGACT-TACTGACAACTGGTTCGACCCC.

Nucleotide sequence of the FR4 of the heavy chain of human monoclonal antibodies F431 and COMB (i.e., SEQ ID NO:48): TGGGGCCAGGGAACCCTGGTCAC-CGTCTCCTCA.

Single amino acid sequence of the variable region of the heavy chain of human monoclonal antibodies F431 and COMB specific to the *P. aeruginosa* MEP antigen (i.e., SEQ ID NO:8):

QLHLQESGPGLVKPSETLSLTCTVSGGPITSNNYYWGWIRQPPGKGLEWI

GTISYNGYTYYIPSLRGRVTISGDTSKNQFSLRVNSVTAADTAMYYCARH

DYSMSSGLTDNWFDPWGQGTLVTVSS.

Single amino acid sequence of FR1 of the heavy chain of human monoclonal antibodies F431 and COMB specific to the *P. aeruginosa* MEP antigen (i.e., SEQ ID NO:61): QLHLQESGPGLVKPSETLSLTCTVSGGPIT.

Single amino acid sequence of CDR1 of the heavy chain of human monoclonal antibodies F431 and COMB specific to the *P. aeruginosa* MEP antigen (i.e., SEQ ID NO:30): SNNYYWG.

Single amino acid sequence of FR2 of the heavy chain of human monoclonal antibodies F431 and COMB specific to the *P. aeruginosa* MEP antigen (i.e., SEQ ID NO:62): WIRQPPGKGLEWIG.

Single amino acid sequence of CDR2 of the heavy chain of human monoclonal antibodies F431 and COMB specific to the *P. aeruginosa* MEP antigen (i.e., SEQ ID NO:31): TISYNGYTYYIPSLRG.

Single amino acid sequence of FR3 of the heavy chain of human monoclonal antibodies F431 and COMB specific to the *P. aeruginosa* MEP antigen (i.e., SEQ ID NO:63): RVTISGDTSKNQFSLRVNSVTAADTAMYYCAR.

Single amino acid sequence of CDR3 of the heavy chain of human monoclonal antibodies F431 and COMB specific to the *P. aeruginosa* MEP antigen (i.e., SEQ ID NO:32): HDYSMSSGLTDNWFDP.

Single amino acid sequence of FR4 of the heavy chain of human monoclonal antibodies F431 and COMB specific to the *P. aeruginosa* MEP antigen (i.e., SEQ ID NO:64): WGQGTLVTVSS.

Example 2

Materials and Methods:

Binding Assays to *P. aeruginosa* and purified MEP: ELISA plates were coated with purified *P. aeruginosa* MEP at 2 μg/ml in 0.02 M phosphate buffer containing sodium azide overnight at 4° C. The plates were washed several times to remove unbound MEP in PBS with 0.05% Tween. The plates were then incubated overnight at 4° C. with PBS/BSA in order to block all other non-specific binding sites. Following several washes, antibodies were added to the plates at various concentrations ranging from 0.0625 to 2.0 μg/ml. The plates were incubated for 2 hours at room temperature. Bound antibody was detected with an alkaline phosphatase conjugated goat anti-human IgG antibody specific for the Fc domain. Assays could similarly be performed using intact bacteria, as described by Preston et al. Infection and Immunity 66:4137–4142, 1998.

Complement Deposition Assays: ELISA plates were coated with purified *P. aeruginosa* MEP at a concentration of 10 μg/ml in 0.02 M phosphate buffer at pH 7, at room temperature, overnight (e.g., approximately 10 hours). Antibodies were added at various concentrations and the plates were incubated for 1 hour at 37° C. Normal human serum was added as a source of complement. The plates were further incubated for 15 minutes and then washed and incubated with polyclonal rabbit anti-human C3 antiserum. Rabbit antibodies that bound to C3 were detected using alkaline phosphatase conjugated goat anti-rabbit IgG. The OD405 was measured after incubation for 45 minutes at room temperature.

Opsonophagocytic Killing Assays: Opsonophagocytic killing assays have been described previously. (See Ames et al. Infection and Immunity 49:281–285, 1985.) Briefly, assays are carried out in the presence of 10% heat-inactivated fetal bovine serum, and fresh human serum is used as a complement source at a 1:10 dilution. The serum is pre-exposed to for 30 minutes on ice to P. aeruginosa in order to remove any pre-existing P. aeruginosa specific antibodies. The assay was carried out by mixing 100 µl of bacteria at $2 \times 10^7$ bacteria/ml, 100 µl of different dilutions of the test antibody, 100 µL of purified fresh human polymorphonuclear leukocytes (PMN) at $2 \times 10^7$ cells/ml as a source of phagocytic cells, and 100 µl of absorbed serum as a complement source. Controls lacked PMNs. The test and control tubes were incubated for 60 minutes at 37° C. with constant agitation. To test for lysis, aliquots were removed, diluted and cultured in agar plates. Following overnight incubation, the plates were scored for colony growth. The percent reduction in the colony forming units (CFU) relative to that in control assay tubes was calculated as follows:

[(CFU surviving in the absence of PMNs–CFU surviving in the presence of PMNs)/CFU surviving in the absence of PMNs]×100.

In Vivo Bacterial Challenge Survival Assays:

Mice were anesthetized using ketamine and xylamine, and then administered 50 µg of either control or test monoclonal antibody (F429γ1 and FCOMBγ1) by intranasal instillation at 4 hours prior to challenge. Mice were then challenged with live P. aeruginosa strain N13 ($5 \times 10^7$ cfu/mouse) by the same route of administration as antibody. Survival was measured up to five days after challenge.

Results:

All the antibodies tested were able to bind to MEP, albeit with different affinities. At the highest concentration of antibody tested (2.0 µg/ml), FCOMBγ1 was able to bind MEP to the greatest degree (FIG. 1). The affinities of the other antibodies at this concentration were (in decreasing order) F431γ1, F428γ1, and F429γ1. At the lowest concentration of antibody tested (0.0625 µg/ml), the F431γ1 showed the greatest affinity. The affinities of the other antibodies at this lower concentration were (in decreasing order) FCOMBγ1, F428γ1, and F429γ1.

Figure 2:
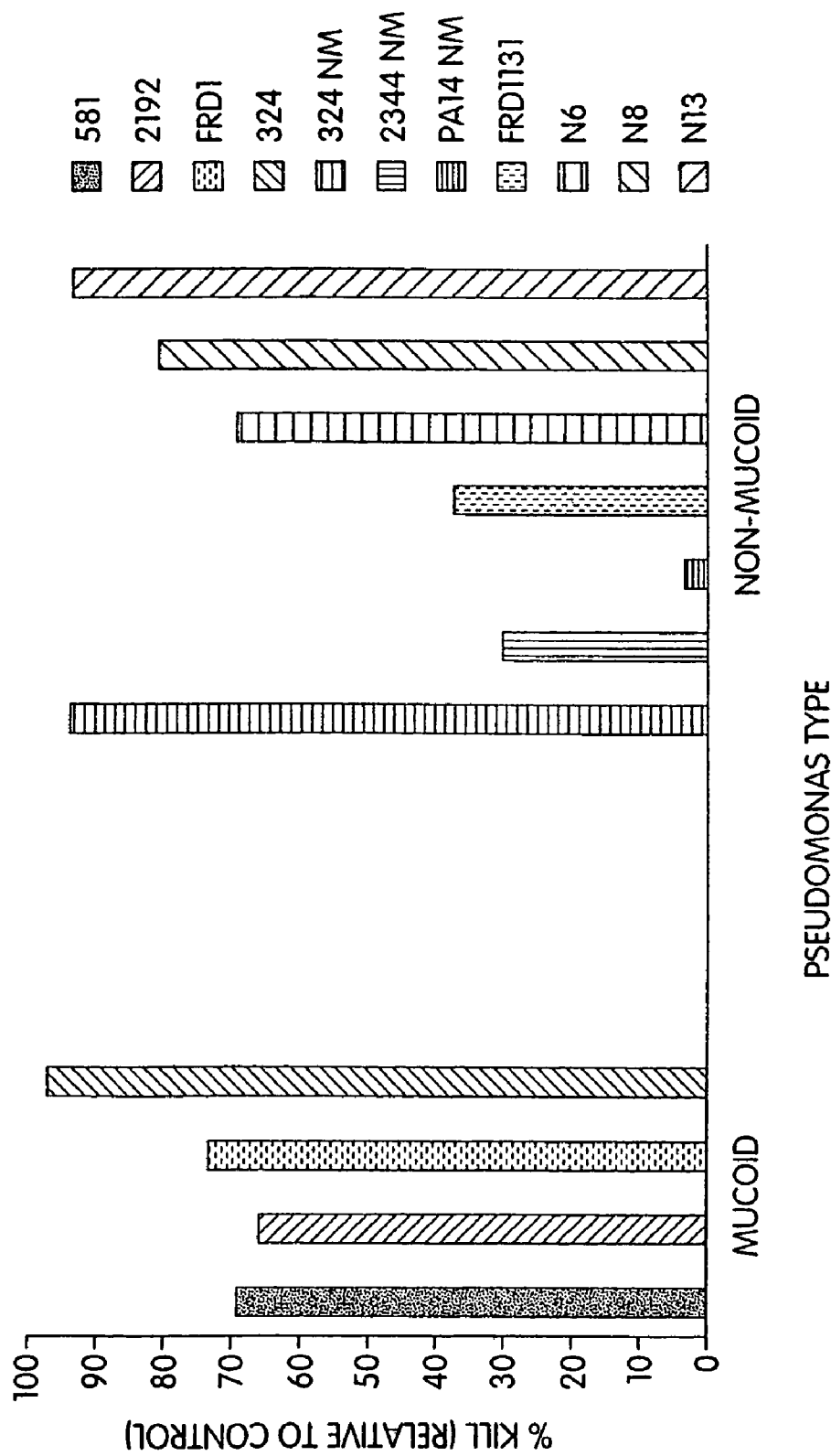
FIG. 2 is a bar graph showing opsonic killing of mucoid and non-mucoid *P. aeruginosa* strains by the monoclonal antibody F429γ1 at concentrations of 4–25 μg.

The ability of F429γ1 to induce opsonic killing of eleven different mucoid and non-mucoid P. aeruginosa strains was analyzed (FIG. 2). Four mucoid strains (581, 2192, FRD1, and 324) and seven non-mucoid strains (324 NM, 2344 NM, PA14 NM, FRD1131, N6, N8, and N13) were used. F429γ1 was used at a concentration ranging from 4–25 µg per assay. The antibody was able to induce at least 60% killing (as compared to a control which lacked any antibody) for each mucoid strain tested. It was similarly able to induce at least 60% killing in four of the seven non-mucoid strains tested (324 NM, N6, N8, and N13). In two of the seven non-mucoid strains (2344 NM and FRD1131), F429γ1 was able to induce at least 25% killing. The remaining non-mucoid strain (PA14 NM) was relatively resistant to killing by F429γ1, with less than 5% killing observed. These results indicate that the F429γ1 antibody is able to recognize and induce opsonic killing of mucoid and non-mucoid strains.

Figure 3:
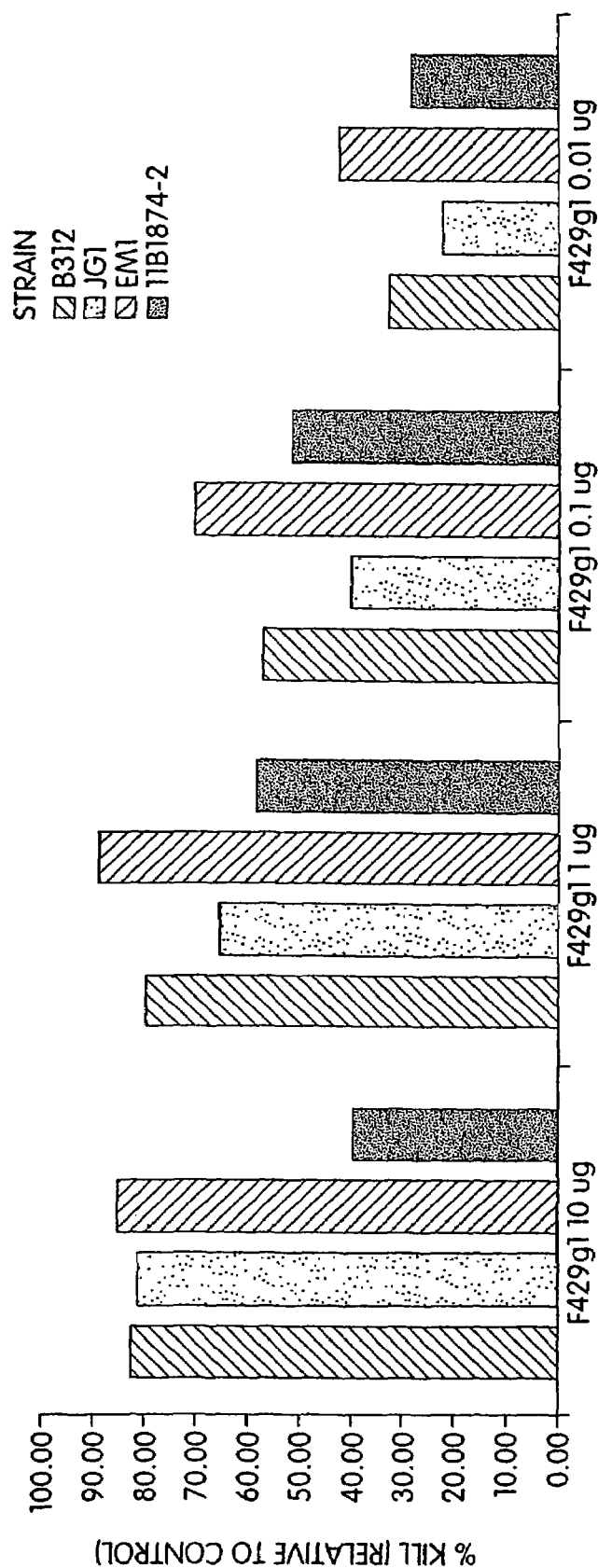
FIG. 3 is a bar graph showing opsonic killing of *P. aeruginosa* strains isolated from bacteremic patients as a function of monoclonal antibody F429γ1 concentration.

To test the ability of F429γ1 to induce opsonic killing of natural isolates of P. aeruginosa, four P. aeruginosa strains were recovered from the blood of bacteremic patients and the susceptibility to F429γ1-induced opsonic killing was tested (FIG. 3). F429γ1 was used at concentrations ranging from 0.01 µg to 10.0 µg. The four isolates used were B312, JG1, EM1, and 11B1874-2. A concentration dependent effect was observed for all isolates. At the lowest dose of F429γ1 (0.01 µg), the antibody was effective at inducing at least 20% killing for all isolates. When used at 1.0 µg, the antibody was able to induce at least 55% kill in all the isolates, with two of the isolates demonstrating greater susceptibility to the antibody (B312 and EM1).

Figure 4:
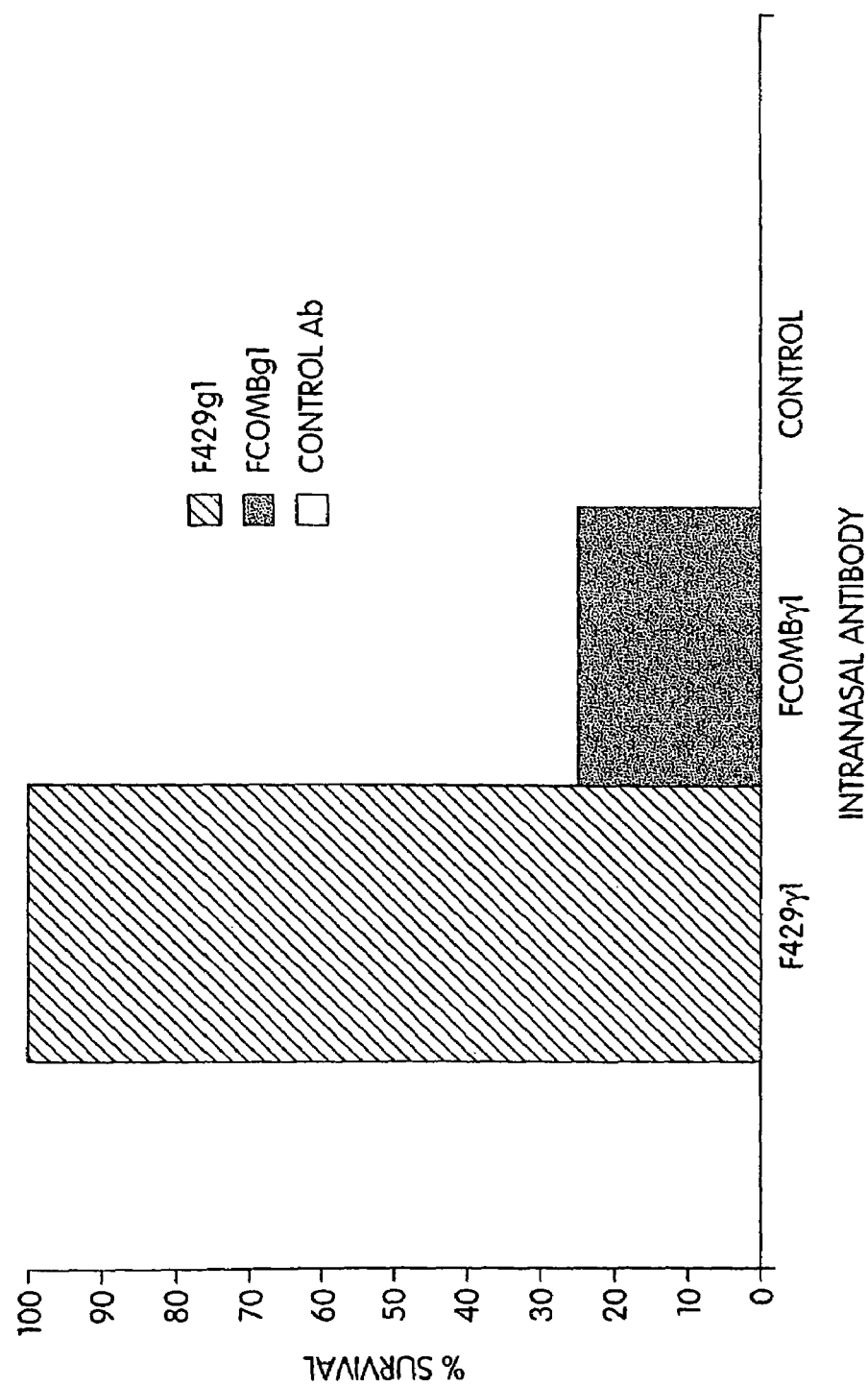
FIG. 4 is a bar graph showing the effects of antibody administration on mouse survival following challenge with live *P. aeruginosa* bacteria.

To test the efficacy of the antibodies in vivo, F429γ1 and FCOMBγ1 were administered to murine subjects by intranasal instillation (50 µg) followed by challenge with live P. aeruginosa strain N13 (FIG. 4). Survival was monitored for up to five days after challenge. FIG. 4 shows the survival curve of mice following challenge. None of the mice administered control antibody, about 25% of animals administered FCOMBγ1, and 100% of animals administered F429γ1 survived the challenge with strain N13. These data show that both F429γ1 and FCOMBγ1 impart protection to mice challenged with P. aeruginosa, although F429γ1 was more effective than FCOMBγ1.

EQUIVALENTS

The foregoing written specification is to be considered to be sufficient to enable one skilled in the art to practice the invention. The particular antibodies and peptides disclosed herein are not to be construed as limiting of the invention as they are intended merely as illustrative of particular embodiments of the invention as enabled herein. Therefore, any peptides, antibodies, and antibody fragments that are functionally equivalent to those described herein are within the spirit and scope of the claims appended hereto. Indeed, various modifications of the invention in addition to those shown and described herein will become apparent to those skilled in the art from the foregoing description and fall within the scope of the appended claims.

All references, patents and patent publications that are recited in this application are incorporated in their entirety herein by reference.

We claim:

1. A composition, comprising an isolated peptide that selectively binds to *P. aeruginosa* mucoid exopolysaccharide and comprises an amino acid sequence selected from the group consisting of SEQ ID NO:5 and SEQ ID NO:8 or a variant having at least 95% identity to SEQ ID NO:5 or SEQ ID NO:8.

2. The composition of claim 1, wherein the isolated peptide comprises amino acid sequence SEQ ID NO:5.

3. The composition of claim 1, wherein the isolated peptide comprises amino acid sequence SEQ ID NO:8.

4. The composition of claim 1, wherein the isolated peptide is an isolated antibody or antibody fragment.

5. The composition of claim 4, wherein the isolated antibody or antibody fragment is an intact soluble monoclonal antibody.

6. The composition of claim 4, wherein the isolated antibody or antibody fragment is an isolated monoclonal antibody fragment selected from the group consisting of an F(ab')₂ fragment, an Fd fragment, and an Fab fragment.

7. The composition of claim 4, wherein the isolated antibody or antibody fragment enhances opsonophagocytosis of *P. aeruginosa*.

8. The composition of claim 4, wherein the isolated antibody or antibody fragment comprises
an amino acid sequence selected from the group consisting of SEQ ID NO:5 and SEQ ID NO:8, and
an amino acid sequence selected from the group consisting of SEQ ID NO:6 and SEQ ID NO:7.

9. The composition of claim 4, wherein the isolated antibody or antibody fragment comprises an amino acid sequence of SEQ ID NO:5 and an amino acid sequence of SEQ ID NO:6.

10. The composition of claim 4, wherein the isolated antibody or antibody fragment comprises an amino acid sequence of SEQ ID NO:5 and an amino acid sequence of SEQ ID NO:7.

11. The composition of claim 4, wherein the isolated antibody or antibody fragment comprises an amino acid sequence of SEQ ID NO:8 and an amino acid sequence of SEQ ID NO:6.

12. The composition of claim 4, wherein the isolated antibody or antibody fragment comprises an amino acid sequence of SEQ ID NO:8 and an amino acid sequence of SEQ ID NO:7.

13. The composition of claim 1, wherein the isolated peptide is conjugated to a detectable label.

14. The composition of claim 1, wherein the composition is a pharmaceutical composition further comprising a pharmaceutically acceptable carrier.

15. The composition of claim 4, wherein the isolated antibody or antibody fragment is present in an effective amount for inhibiting a *P. aeruginosa* infection.

16. The composition of claim 4, wherein the isolated antibody or antibody fragment is present in an effective amount for inhibiting a disorder associated with the presence of *P. aeruginosa* infection.

17. The composition of claim 14, wherein the isolated peptide is present in an effective amount for detecting *P. aeruginosa* in a sample in or from a subject.

18. The composition of claim 4, wherein the isolated antibody or antibody fragment is a human antibody or antibody fragment.

19. A method for detecting *P. aeruginosa* in a subject comprising
determining a test level of binding of the isolated peptide of claim 1 to a sample in or from a subject, and
comparing the test level of binding to a control,
wherein a test level of binding that is greater than the control is indicative of the presence of *P. aeruginosa* in the sample.

20. A method for treating a subject having, or at risk of developing, a *P. aeruginosa* infection comprising
administering to a subject in need of such treatment the isolated peptide of claim 1 in an amount effective to inhibit a *P. aeruginosa* infection.

21. The composition of claim 4, wherein the isolated antibody or antibody fragment is an IgG, IgA or IgM isotype.

22. The composition of claim 4, wherein the isolated antibody fragment is an Fv.

23. A composition, comprising an isolated peptide that selectively binds to *P. aeruginosa* mucoid exopolysaceharide and comprises an amino acid sequence selected from the group consisting of SEQ ID NO:6 and SEQ ID NO:7 or a variant having at least 95% identity to SEQ ID NO:6 or SEQ ID NO:7.

24. The composition of claim 23, wherein the isolated peptide comprises amino acid sequence SEQ ID NO:6.

25. The composition of claim 23, wherein the isolated peptide comprises amino acid sequence SEQ ID NO:7.

26. The composition of claim 23, wherein the isolated peptide is an isolated antibody or antibody fragment.

27. The composition of claim 26, wherein the isolated antibody or antibody fragment is an intact soluble monoclonal antibody.

28. The composition of claim 26, wherein the isolated antibody or antibody fragment is an isolated monoclonal antibody fragment selected from the group consisting of an F(ab')$_2$ fragment, an Fd fragment, and an Fab fragment.

29. The composition of claim 26, wherein the isolated antibody or antibody fragment enhances opsonophagocytosis of *P. aeruginosa*.

30. The composition of claim 23, wherein the isolated peptide is conjugated to a detectable label.

31. The composition of claim 23, wherein the composition is a pharmaceutical composition further comprising a pharmaceutically acceptable carrier.

32. The composition of claim 26, wherein the isolated antibody or antibody fragment is present in an effective amount for inhibiting a *P. aeruginosa* infection.

33. The composition of claim 26, wherein the isolated antibody or antibody fragment is present in an effective amount for inhibiting a disorder associated with the presence of *P. aeruginosa* infection.

34. The composition of claim 31, wherein the isolated peptide is present in an effective amount for detecting *P. aeruginosa* in a sample in or from a subject.

35. The composition of claim 26, wherein the isolated antibody or antibody fragment is a human antibody or antibody fragment.

36. The composition of claim 26, wherein the isolated antibody or antibody fragment is an IgG, IgA or IgM isotype.

37. A method for detecting *P. aeruginosa* in a subject comprising
determining a test level of binding of the isolated peptide of claim 23 to a sample in or from a subject, and
comparing the test level of binding to a control,
wherein a test level of binding that is greater than the control is indicative of the presence of *P. aeruginosa* in the sample.

38. A method for treating a subject having, or at risk of developing, a *P. aeruginosa* infection comprising
administering to a subject in need of such treatment the isolated peptide of claim 23 in an amount effective to inhibit a *P. aeruginosa* infection.

39. The composition of claim 23, wherein the isolated antibody fragment is an Fv.

* * * * *

UNITED STATES PATENT AND TRADEMARK OFFICE
CERTIFICATE OF CORRECTION

PATENT NO. : 7,119,172 B2 Page 1 of 1
APPLICATION NO. : 10/440522
DATED : October 10, 2006
INVENTOR(S) : Gerald B. Pier et al.

It is certified that error appears in the above-identified patent and that said Letters Patent is hereby corrected as shown below:

On the title of the patent, at item (75), for Michael J. Preston, delete "Alan, ME" and insert -- Alna, ME --.

In column 63, line 26-27 claim 23, delete "exopolysace-haride " and insert -- exopolysaccharide --

Signed and Sealed this

Twenty-sixth Day of December, 2006

JON W. DUDAS
*Director of the United States Patent and Trademark Office*